United States Patent
Van Valkenburgh et al.

(10) Patent No.: US 7,553,146 B2
(45) Date of Patent: *Jun. 30, 2009

(54) APPARATUS FOR MAKING AIR-LAID STRUCTURES

(75) Inventors: Curtis Hunter Van Valkenburgh, Mason, OH (US); Claudio Antonio Matos, Belleville (CA); Karen Juliana Fegelman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 231 days.

This patent is subject to a terminal disclaimer.

(21) Appl. No.: 11/599,789

(22) Filed: Nov. 15, 2006

(65) Prior Publication Data
US 2008/0113052 A1    May 15, 2008

(51) Int. Cl.
  B29C 41/32 (2006.01)
  B29C 41/40 (2006.01)
  A61F 13/15 (2006.01)
(52) U.S. Cl. .................. 425/80.1; 425/81.1; 425/82.1; 425/83.1; 425/215
(58) Field of Classification Search ............. 425/72.1, 425/72.2, 80.1, 81.1, 82.1, 83.1, 468, 470, 425/DIG. 2, 215; 264/37.1, 37.17, 37.28, 264/39, 101–103, 112, 119, 121, 211.12, 264/324, 510, 511, 553, 555, 571, 517, 518; 19/144, 145, 148, 308
See application file for complete search history.

(56) References Cited

U.S. PATENT DOCUMENTS 3,518,726 A * 7/1970 Banks .................. 28/121
3,873,259 A * 3/1975 Kennedy ................ 425/470
3,973,291 A   8/1976 Kolbach
4,005,957 A * 2/1977 Savich .................. 425/80.1

(Continued)

FOREIGN PATENT DOCUMENTS

FR  2 690 843   11/1993

(Continued)

OTHER PUBLICATIONS

U.S. Appl. No. 11/599,821, filed Nov. 15, 2006, C. A. Matos et al.

(Continued)

*Primary Examiner*—Philip C Tucker
*Assistant Examiner*—Dimple N Bodawala
(74) *Attorney, Agent, or Firm*—Gary J. Foose

(57) ABSTRACT

An apparatus for forming air-laid fibrous articles. The apparatus can have a core pocket. The core pocket can have a shield. The core pocket can further have a central opening defined by a void in the shield. The core pocket can further have a central forming chamber in air-flow communication with the central opening and having a central forming chamber periphery. The core pocket can further have a central foraminous forming surface in air-flow communication with the central forming chamber. The core pocket can further have a pair of edge openings extending along the shield. The core pocket can further have an edge forming chamber disposed about the central forming chamber periphery and in air-flow communication with the edge openings. The core pocket can further have an edge foraminous forming surface in air-flow communication with the edge forming chamber.

20 Claims, 11 Drawing Sheets

U.S. PATENT DOCUMENTS

| | | | |
|---|---|---|---|
| 4,388,056 A | 6/1983 | Lee et al. | |
| 4,592,708 A | 6/1986 | Feist et al. | |
| 4,666,647 A | 5/1987 | Enloe et al. | |
| 4,674,966 A | 6/1987 | Johnson et al. | |
| 4,761,258 A | 8/1988 | Enloe | |
| 4,859,388 A | 8/1989 | Peterson et al. | |
| 4,888,231 A | 12/1989 | Angstadt | |
| 4,904,440 A | 2/1990 | Angstadt | |
| 4,995,141 A * | 2/1991 | Gould | 19/148 |
| 5,004,579 A | 4/1991 | Wislinski et al. | |
| 5,447,677 A | 9/1995 | Griffoul et al. | |
| 5,866,173 A * | 2/1999 | Reiter et al. | 425/80.1 |
| 6,098,249 A * | 8/2000 | Toney et al. | 19/296 |
| 6,146,580 A | 11/2000 | Bontaites, Jr. | |
| 6,330,735 B1 * | 12/2001 | Hahn et al. | 19/296 |
| 6,416,697 B1 * | 7/2002 | Venturino et al. | 264/113 |
| 6,461,086 B1 * | 10/2002 | Milanowski et al. | 406/92 |
| 6,497,009 B2 * | 12/2002 | Geisen et al. | 19/296 |
| 6,627,130 B2 * | 9/2003 | Kugler et al. | 264/118 |
| 6,630,088 B1 | 10/2003 | Venturino et al. | |
| 6,630,096 B2 | 10/2003 | Venturino et al. | |
| 6,652,798 B1 | 11/2003 | Edvardsson | |
| 6,736,923 B1 | 5/2004 | Franzmann et al. | |
| 6,811,642 B2 | 11/2004 | Ochi | |
| 6,846,448 B2 * | 1/2005 | Rymer et al. | 264/460 |
| 6,989,118 B2 | 1/2006 | Venturino et al. | |
| 7,001,167 B2 * | 2/2006 | Venturino et al. | 425/80.1 |
| 7,094,373 B2 * | 8/2006 | Heyn et al. | 264/101 |
| 7,157,033 B2 * | 1/2007 | Kuchenbecker et al. | 264/162 |
| 7,204,682 B2 * | 4/2007 | Venturino et al. | 425/82.1 |
| 2002/0013112 A1 | 1/2002 | Bontaites, Jr. et al. | |
| 2002/0070471 A1 | 6/2002 | Lee et al. | |
| 2004/0023583 A1 | 2/2004 | Venturino et al. | |
| 2004/0061264 A1 * | 4/2004 | Heyn et al. | 264/518 |
| 2008/0113054 A1 * | 5/2008 | Fegelman et al. | 425/81.1 |

FOREIGN PATENT DOCUMENTS

WO    WO 2005/072671 A1    8/2005

OTHER PUBLICATIONS

U.S. Appl. No. 11/599,820, filed Nov. 15, 2006, K. J. Fegelman et al.
U.S. Appl. No. 11/599,843, filed Nov. 15, 2006, C. H. Van Valkenburgh et al.
PCT International Search Report dated Jul. 21, 2008.

* cited by examiner

APPARATUS FOR MAKING AIR-LAID STRUCTURES

FIELD OF THE INVENTION

The present invention relates to an apparatus for making air-laid articles.

BACKGROUND OF THE INVENTION

Air-laid structures are widely used in the art of absorbent articles and other arts in which fibrous webs are of use. One common approach for creating air-laid structures is to process a fibrous sheet of cellulosic fibers or other suitable fibers through a device that breaks up the fibrous sheet, thereby forming discrete fibers. The discrete fibers are entrained in a stream of air and directed to a foraminous forming surface upon which the fibers are deposited to form fluff. Typically, fluff has a high porosity and is comprised of essentially randomly oriented fibers. In some processes, a vacuum is applied to one side of the foraminous surface to create a pressure differential across the foraminous forming surface to assist with drawing the discrete fibers to the foraminous forming surface.

Absorbent articles such as sanitary napkins, diapers, and adult incontinence products commonly employ air-laid structures in the absorbent core. Absorbent cores have a generally planar structure in which the thickness is generally smaller than the planar dimensions. One common approach to forming air-laid absorbent articles is to situate the foraminous surface in a recess. In the art, the structure in which the foraminous surface is emplaced and the foraminous surface are components of what is commonly referred to as a core pocket. The thickness can be partially controlled by the depth of the recess in the core pocket and the planar dimensions of the absorbent core can be defined by the dimensions of the recess and the foraminous surface Absorbent cores having a variable thickness are thought to fit wearers better and to have better fluid acquisition properties. Absorbent cores in which the thickness of the absorbent core varies can be created by using a foraminous surface that is contoured in the thickness dimension. Thus, different quantities of fibers are required to fill different portions of the core pocket. One problem with filling a contoured foraminous surface to form an absorbent core having variable thickness is that a substantial amount of scarfing may need to be performed on the core to render the core flat on the side of the pad opposing the contoured side, which is the typical construction of many types of absorbent cores. For absorbent cores such as those used in sanitary napkins, the contoured side can be the body facing surface and a flat garment facing side can be desired or vice versa.

During formation of the article, the fibers filling a core pocket having a foraminous surface that is contoured in the thickness dimension can be thought of as being like snow falling in a ditch. When enough snow has fallen such that the level of snow in the deepest portion of the ditch is even with the level of the ground surrounding the ditch, the level of the snow above the shallower edges of the ditch will be above the level of the surface of the ground surrounding the ditch. Thus, to make the level of snow in the ditch even or flat, snow above the shallower edges of the ditch needs to be scarfed away to be even with the level of snow in the deepest portion of the ditch. An analogous situation arises in air laying fibrous articles having a contoured thickness in which one surface is desired to be flat.

Scarfing imparts mechanical energy to the fibrous articles which can result in uncontrollable changes in the basis weight and structure of the fibrous articles. Many designers of absorbent articles recognize that small variations in the basis weight and structure of absorbent cores can have significant impacts on the fluid acquisition and retention properties of absorbent articles. Uncontrolled variations in basis weight within a single absorbent core and uncontrolled variations in basis weight between multiple absorbent cores formed on a single manufacturing line can be unacceptable to manufacturers of absorbent articles because consumers demand that absorbent articles sold under a particular brand name perform consistently. Furthermore, scarfing can result in wasted fibrous material and if the scarfed fibrous material is recycled, some of the fibers can be damaged by scarfing.

Absorbent cores having a basis weight that varies in plane can be desirable. The partially saturated fluid acquisition and retention properties of air-laid absorbent cores are known to vary as a function of basis weight. For instance, some designers of absorbent articles designed to be worn close to the human body desire an absorbent core in which the basis weight of the center of the absorbent core is greater than the basis weight of the periphery of the absorbent core. For some designs of absorbent articles, precise variations in basis weight in the machine direction and cross direction can be helpful with achieving optimum performance of the absorbent article.

With these limitations in mind, the problem remains with providing an apparatus to manufacture air-laid fibrous articles in which the basis weight can vary in plane. There is a further unmet need for providing an apparatus in which the variation in the basis weight in the machine direction and cross direction can be precisely controlled. There is an additional unmet need for an apparatus for forming air-laid fibrous articles in which the amount of excess fibrous material deposited is minimized.

SUMMARY OF THE INVENTION

An apparatus for forming air-laid fibrous articles is disclosed. The apparatus can comprise a core pocket. The core pocket can comprise a shield having an interior facing surface, an exterior facing surface, a shield first end, a shield second end opposing the shield first end, and a pair of opposing shield lateral side edges extending from the shield first end to the shield second end. The core pocket can further comprise a central opening defined by a void in the shield. The core pocket can further comprise a central forming chamber in air-flow communication with the central opening and having a central forming chamber periphery. The core pocket can further comprise a central foraminous forming surface in air-flow communication with the central forming chamber. The core pocket can further comprise a pair of edge openings extending along the shield and extending laterally beyond the shield lateral side edges. The core pocket can further comprise an edge forming chamber disposed about the central forming chamber periphery and in air-flow communication with the edge openings. The core pocket can further comprise an edge foraminous forming surface in air-flow communication with the edge forming chamber.

The core pocket can further comprise a plurality of central lateral baffles. The central lateral baffles can span the central forming chamber. The central lateral baffles can be aligned about flush with the interior facing surface of the shield.

The core pocket can be considered to have a machine direction. The core pocket can further comprise a plurality of edge lateral baffles. The edge lateral baffles can span the edge forming chamber. The edge lateral baffles can be aligned about flush with the interior facing surface of the shield.

The shield can be generally rectangular. The pair of edge openings can extend from the shield first end to the shield second end.

A portion of the central foraminous forming surface can be recessed relative to the edge foraminous forming surface.

The apparatus can further comprise an air-distribution manifold operatively related to the core pocket. The air-distribution manifold can comprise a central zone. The central zone can have a central zone first end, a central zone second end opposing the central zone first end, a pair of opposing central zone lateral side edges extending from the central zone first end to the central zone second end, and a pair of edge zones adjacent the central zone lateral side edges. The pressure in the central zone can be negative and less than the pressure in the edge zones.

Each edge zone can have an edge zone first end and an edge zone second end opposing the edge zone first end. Each edge zone first end can be aligned with the central zone first end. Each edge zone second end can be aligned with the central zone second end.

The air-distribution manifold can further comprise a central recycle zone. The central recycle zone can have a central recycle zone first end, a central recycle zone second end opposing the central recycle zone first end, and a pair of opposing central recycle zone lateral side edges extending from the central recycle zone first end to the central recycle zone second end, wherein the central recycle zone first end is adjacent the central zone second end.

The edge zone first end can be aligned with the central zone first end and the edge zone second end can be aligned with the central recycle zone second end.

The air-distribution manifold can further comprise a central scarfing zone. The central scarfing zone can have a central scarfing zone first end, a central scarfing zone second end opposing the central scarfing zone first end, and a pair of opposing central scarfing zone lateral side edges extending from the central scarfing zone first end to the central scarfing zone second end, wherein the central scarfing zone first end can be adjacent the central recycle zone second end.

The air-distribution manifold can further comprise a pair of edge scarfing zones adjacent the central scarfing zone lateral side edges. Each edge scarfing zone can have an edge scarfing zone first end and an edge scarfing zone second end opposing the edge scarfing zone first end, wherein the edge scarfing zone first end is aligned with the central scarfing zone first end. The edge scarfing zone second end can be aligned with the central scarfing zone second end.

The apparatus can further comprise a scarfing roll positioned in operative relationship with the central scarfing zone. The apparatus can further comprise a recycle duct having a recycle duct entrance and a recycle duct exit. The recycle duct entrance can be positioned in operative relationship with the scarfing roll and the recycle duct exit can be positioned in operative relationship with the central recycle zone. The air-distribution manifold can have air-distribution surface that is curved. The core pocket can be shaped to form an absorbent article designed to be worn in proximity to the crotch of the wearer.

DETAILED DESCRIPTION OF THE INVENTION

Figure 1:
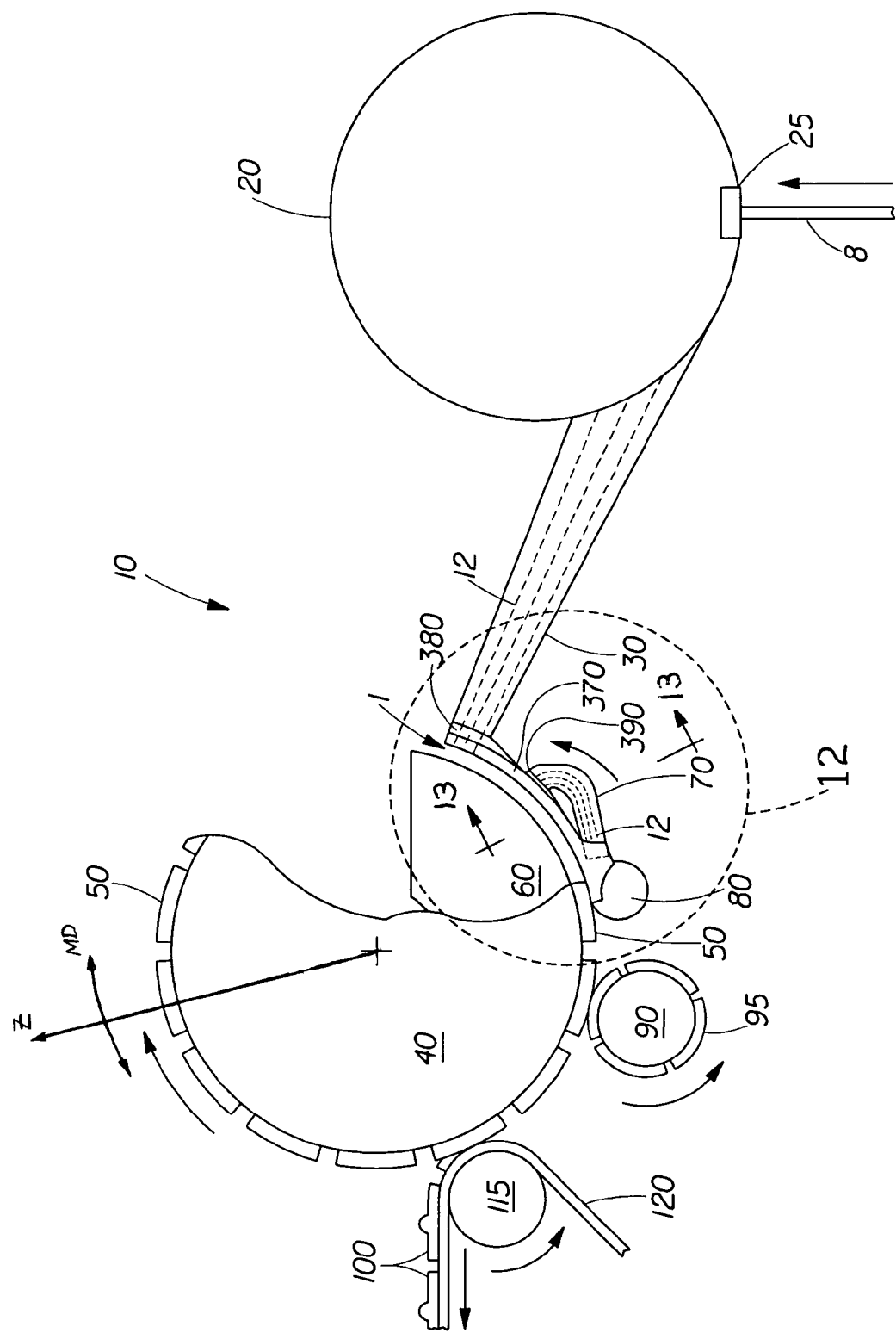
FIG. 1 is an illustration of a side view of one embodiment of an apparatus for forming air-laid fibrous articles.

An illustration of one embodiment of an apparatus 10 for forming air-laid fibrous articles is shown in FIG. 1. The apparatus 10 can comprise a hammermill 20, or other suitable apparatus such as a disk mill or lickerin or other apparatus for disassociating fibers of a drylap web, into which a drylap web 8 can be fed through an infeed slot 25. The hammermill 20 disassociates the fibers of the drylap web and then discharges a relatively high velocity stream of loose air-entrained fibers 12 that is directed through discharge chute 30 generally towards a core pocket 50. A fiber source entrance chamber 380 can be connected to the discharge chute 30 to assist with distributing the fibers over the core pocket 50. One or more core pockets 50 can be disposed in a circumferential relationship about the periphery of deposition drum 40. The core pockets 50 can have a foraminous forming surface. Deposition drum 40 can rotate about air-distribution manifold 60. Air-distribution manifold 60 can be in air-flow communication with one or more core pockets 50 as deposition drum 40 rotates about air-distribution manifold 60. As the core pocket 50 rotates near or past the discharge chute 30, air-distribution manifold 60 can apply a vacuum to at least a portion of the core pocket 50. The vacuum combined with the momentum of the fibers 12 discharged through discharge chute 30 act to draw and direct, respectively, the air-entrained fibers 12 into at least a portion of the core pocket 50 as the core pocket 50 rotates about air-distribution manifold 60 through a region near or past the discharge chute 30. As the air-entrained fibers impinge upon the foraminous forming surfaces of the core pocket 50, the fibers are retained on the foraminous forming surfaces and the air passes through the foraminous forming surface. Other embodiments of the apparatus 10 are possible in which the air-distribution manifold 60 has a different shape from that shown in FIG. 1 and the core pockets 50 are moved across air-distribution manifold 60 by other means. For instance, the air-distribution manifold 60 may have a flat surface and the core pockets having a flat surface may be slid across the air-distribution manifold 60 by a conveyor system. The core pocket 50 can be described as being in slideable and sealable engagement with the air-distribution manifold 60.

Non-fibrous materials can be used in place of the fibers 12 provided that the non-fibrous materials used can be conveyed or directed by the flow of air. Non-fibrous materials can include, but are not limited to, pellets, powders, chunks, and shreds of non-fibrous materials.

The core pocket 50 can be slightly overfilled. Scarfing roll 80 can be used to scarf excess fibers 12 deposited in the core pocket 50. A recycle duct 70 can be included in the apparatus 10 to transport excess fibers 12 removed by scarfing. The recycle duct 70 can be configured to transport excess fibers upstream in the process to a recycle distribution chamber 390 which provides a stream of recycled loose air-entrained fibers to be distributed and redeposited in a core pocket 50.

A lugged cylinder 90 can also be an element of the apparatus 10. A plurality of lugs 95 can be disposed about the lugged cylinder 90. The lugs 95 can compact the mass of fibers 12 deposited in the core pocket 50 to complete formation of the air-laid fibrous article 100. The formed air-laid fibrous articles 100 can be removed from the apparatus by a takeaway conveyor comprising a vacuum type return roll 115 and a belt 120. The vacuum type return roll 115 can pull the air-laid fibrous articles 100 from the core pockets 50 as the core pocket 50 rotates past the vacuum type return roll 115.

The apparatus 10 can have a single source of fibers 12 in which a stream of air-entrained fibers can be directed towards the core pocket 50. The apparatus 10 can have a single forming zone 1 in proximity to a single source of fibers 12, the forming zone being the portion of the apparatus 10 in which fibers 12 are deposited in the core pocket 50 from a single source of fibers.

The apparatus 10 can further comprise forming zone shields 370. Forming zone shields 370 can be configured such that as the core pocket 50 moves through the forming zone 1, the amount of air flow into the core pocket 50 from the surrounding environment is negligible. In other words, the core pocket 50 can be described as being in slideable and sealable engagement with the forming zone shields 370. Forming zone shields 370 are described more fully herein.

The core pocket 50, and the elements thereof, can be considered to have a machine direction MD. The machine direction can be understood to be the direction in which the core pocket 50 travels as air-laid fibrous articles 100 are formed in the core pocket 50. In the apparatus illustrated in FIG. 1, the machine direction would be in line with the direction of rotation of deposition drum 40. The z direction can be referred to as the direction corresponding with the thickness of the air-laid fibrous article during formation.

U.S. Pat. No. 4,388,056, issued to Lee et al., U.S. Pat. No. 4,859,388, issued to Peterson and Benson, and U.S. Pat. No. 4,592,708 issued to Feist et al. illustrate apparatus for forming air-laid fibrous webs and absorbent articles.

Figure 2:
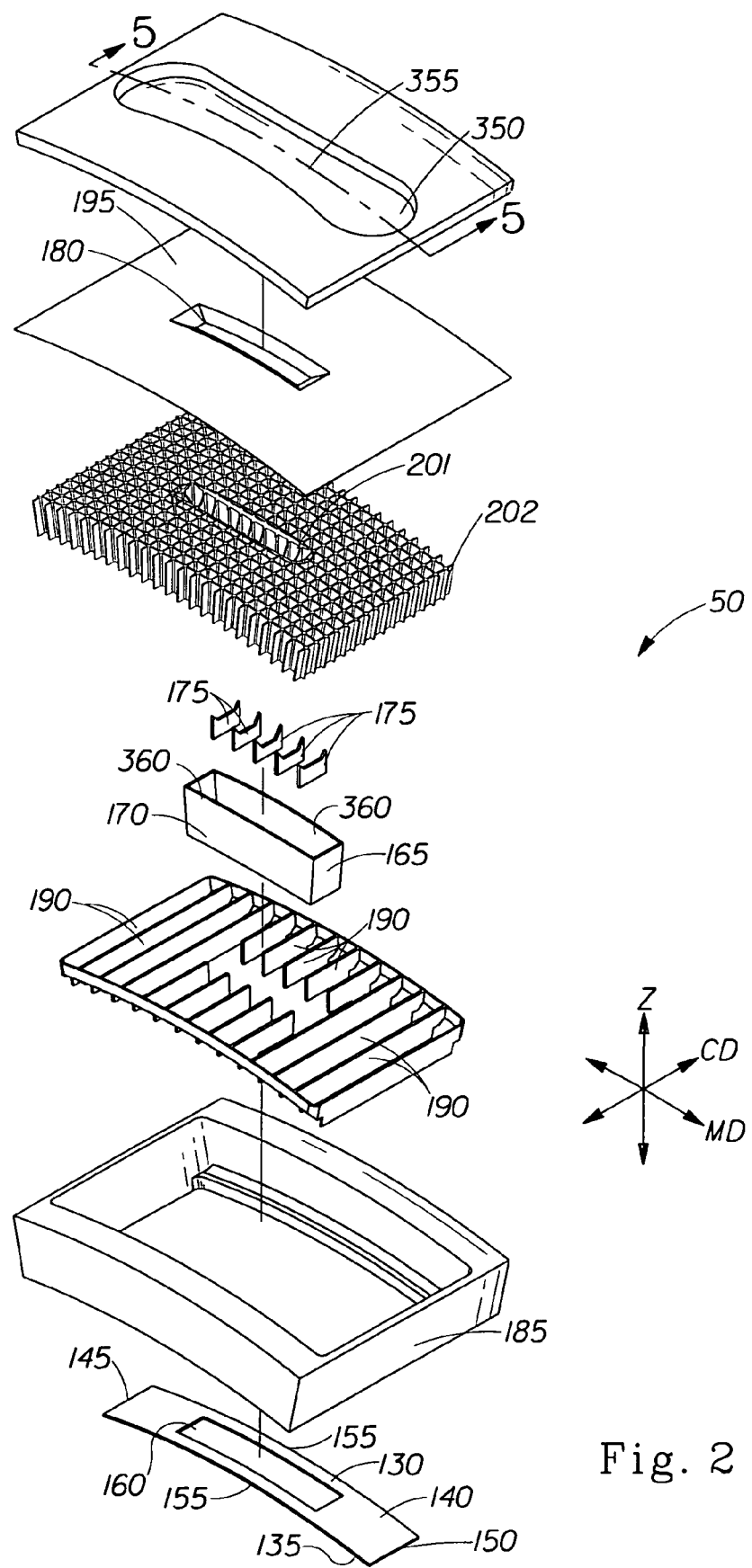
FIG. 2 is an exploded view of a core pocket.

An exploded view of an embodiment of a core pocket 50 is shown in FIG. 2. The core pocket 50, and the elements thereof, can be considered to have a machine direction MD, a cross direction CD, and a z direction generally orthogonal to the MD and CD directions. The cross direction is generally orthogonal to the machine direction and generally in plane with the movement of the core pocket 50 as the core pocket 50 travels during formation of air-laid fibrous articles 100. In the art of air-laid fibrous articles, the z direction can be referred to as the direction corresponding with the thickness of the air-laid fibrous article and the machine direction and cross direction can be considered to be in the plane of the air-laid fibrous article. For an apparatus 10 in which one or more core pockets 50 move circumferentially about air-distribution manifold 60, the z direction is radially orthogonal to the circumferential path of the core pocket 50.

As described herein, the interior facing surfaces or edges are taken to be oriented in a direction away from the discharge chute 30 as the core pocket 50 passes the discharge chute 30. If an air-distribution manifold 60 is present, interior facing surfaces are oriented towards the air-distribution manifold 60 as the core pocket 50 passes the air-distribution manifold 60. The exterior facing surface or edges are taken to be oriented in a direction towards the discharge chute 30 as the core pocket 50 passes the discharge chute 30.

The core pocket 50 can comprise a shield 130 having an interior facing surface 135 and an exterior facing surface 140 opposing the interior facing surface 135. The shield 130 can have a shield first end 145 and a shield second end 150 opposing the shield first end 145. The shield 130 can have a pair of opposing shield lateral side edges 155 each extending from the shield first end 145 to the shield second end 150. The shield 130 can be a sheet of metal, such as stainless steel, titanium, or other material sufficiently stiff to be used in machinery used in high speed manufacturing operations. As illustrated in FIG. 2, the shield 130, and other components illustrated, can have an arcuate shape in the machine direction for use in an apparatus 10 in which the core pockets 50 are disposed in a circumferential relationship about the periphery of deposition drum 40, like that shown in FIG. 1. The shield 130 and other components of the core pocket 50 can be flat in the machine direction if an air-distribution manifold 60 that is flat in the machine direction is used. By way of example, and not to be limiting, the shield can have a width in the cross direction between the shield lateral side edges 155 between about 60 mm and about 110 mm, a length in the machine direction between about 0.15 and about 0.55 radians, and a thickness in the z direction between about 0.5 mm to about 3 mm.

The core pocket 50 can further comprise a central opening 160 defined by a void in the shield. By way of example, and not to be limiting, the central opening 160 can be an approximately rectangular shape having rounded corners and have a length of about 109 mm in the machine direction and width of about 22 mm in the cross direction. Other shapes, lengths, and widths can be practical, the defining feature being that the central opening 160 is sized and dimensioned so as to provide for air-flow communication between the central forming chamber 165 and the air-distribution manifold 60. The length and width of the central opening 160 can be a function of the in-plane geometry of the air-laid fibrous article.

The term air-flow communication is used herein to describe the relationship between two elements in which air flow can be conveyed between, among, across, along, or through the two elements.

The core pocket 50 can further comprise a central forming chamber 165. The central forming chamber 165 can be in air-flow communication with the central opening 160. The central forming chamber 165 can also have a central forming chamber periphery 170. The central forming chamber 165 can be sealed to the shield 130 such that airflow passing between the contacting surfaces of the shield 130 and the central forming chamber 165 can be negligible or nonexistent. The central forming chamber 165 can be formed from stainless steel, titanium, or other material suitable for use in high speed manufacturing operations.

The core pocket 50 can further comprise a plurality of central lateral baffles 175. The central lateral baffles 175 can be nested within the central forming chamber 165. The central lateral baffles 175 can span the central forming chamber 165. That is, the central lateral baffles 175 can extend between the sidewalls 360 of the central forming chamber 165. The central lateral baffles 175 can be aligned about flush with the interior facing surface 135 of the shield 130. The central lateral baffles 175 can be formed from sheets of stainless steel, titanium, or other material suitable for use in high speed manufacturing operations. The sheets can be sized and dimensioned to fit within the central forming chamber 165. The central lateral baffles 175 can be oriented generally orthogonal to the machine direction, as shown in FIG. 2. Embodiments in which the central lateral baffles 175 are not oriented generally orthogonal to the machine direction of the core pocket 50 are also contemplated.

The core pocket 50 can further comprise a central foraminous forming surface 180 in air-flow communication with the central forming chamber 165.

As shown in FIG. 2, the core pocket 50 can further comprise an edge forming chamber 185 that is disposed about the central forming chamber periphery 170. The core pocket 50 can further comprise a plurality of edge lateral baffles 190 nested within the edge forming chamber 185. The edge lateral baffles 190 can span the interior of the edge forming chamber 185. The edge lateral baffles 190 can span the space between the interior boundaries of the edge forming chamber 185 and the boundaries of the central forming chamber 165. The edge lateral baffles 190 can be aligned about flush with the interior facing surface 135 of the shield 130. The edge lateral baffles 190 can be oriented generally orthogonal to the machine direction, as shown in FIG. 2. Embodiments in which the edge lateral baffles 190 are not oriented generally orthogonal to the machine direction of the core pocket 50 are also contemplated. The sheets are sized and dimensioned to fit within the edge forming chamber 185. The edge lateral baffles 190 and central lateral baffles 175 can be formed from sheets of stainless steel, titanium, or other material suitable for use in high speed manufacturing operations.

The central lateral baffles 175 can be spaced apart from one another in the machine direction by about 0.01 to about 0.04 radians. In one embodiment, the central lateral baffles 175 can be spaced apart from one another in the machine direction by about 18 mm. The edge lateral baffles 190 can be spaced apart from one another in the machine direction by about 0.01 to about 0.04 radians. In one embodiment, the edge lateral baffles 190 can be spaced apart from one another in the machine direction by about 18 mm. The edge lateral baffles 190 and central lateral baffles 175 can have a thickness in the MD direction between about 0.5 mm to about 4 mm. The edge lateral baffles 190 and central lateral baffles 175 can have a height in the z direction between about 10 mm and about 40 mm. These dimensions are provided by way of example and not to be limiting, as other dimensions are practical and are a function of the dimensions of the core pocket 50 and materials from which the core pocket 50 is fabricated.

The core pocket 50 can further comprise an edge foraminous forming surface 195 in air-flow communication with the edge forming chamber 185.

The central foraminous forming surface 180 and the edge foraminous forming surface 195 are highly pervious to the flow of air. The central foraminous forming surface 180 and the edge foraminous forming surface 195 can comprise one or more sheets which are permeable to air and have a high percent open area. By way of example, and not to be limiting, the edge foraminous forming surface 195 and central foraminous forming surface 180 can have a percent open area of about 50% percent. The openings in the screen can be about 0.25 mm in diameter. The central foraminous forming surface 180 and the edge foraminous forming surface 195 can be comprised of a thin sheet of stainless steel, titanium, or other material stiff enough to be used in high speed manufacturing operations. The central foraminous forming surface 180 and the edge foraminous forming surface 195 can be comprised of stainless steel, titanium, or other material suitable for use in high speed manufacturing operation having electroetched openings. The central foraminous forming surface 180 and the edge foraminous forming surface 195 can be formed from two or more sheets of foraminous material associated with one another or can be comprised of a single contiguous sheet of foraminous material. WO2001042549A1, filed Dec. 8, 2000 and WO2000029656A1, filed Nov. 17, 1999 describe an embodiment of foraminous forming surfaces.

The edge lateral baffles 190 can span the space between the plane defined by the interior facing surface 135 of the shield 130, which can be flat or curved, and the interior facing surface of the edge foraminous forming surface 195. The central lateral baffles 175 can span the space between a plane defined by the interior facing surface 135 of shield 130 and the interior facing surface of the central foraminous forming surface 180.

The core pocket 50 can optionally comprise a central support mesh 201 adjacent the central foraminous forming surface 180. The core pocket 50 can also optionally comprise an edge support mesh 202 adjacent the edge foraminous forming surface 195. The central support mesh 201 can extend between the central foraminous forming surface 180 and the central lateral baffles 175. The edge support mesh 202 can extend between the edge foraminous forming surface 195 and the edge lateral baffles 190.

The core pocket 50 can optionally comprise a peripheral edge template 350 having a void 355 in the shape of the air-laid fibrous article to be formed. The peripheral edge template 350 can be a separate element attached to the edge forming chamber 185 or can be integral with edge forming chamber 185, such that the edge forming chamber 185 and peripheral edge template 350 are comprised of a unitary material. The peripheral edge template 350 can be positioned adjacent the exterior surface of edge foraminous forming surface 195 in an overlying relationship.

The peripheral edge template 350 can comprise a sheet of material suitable for use in high speed manufacturing operations. The thickness of the peripheral edge template can be selected to correspond with the desired thickness of the air-laid fibrous article 100 in the z direction or a thickness such that the air-laid fibrous article 100 is the proper thickness for further downstream processing. The boundaries of the peripheral edge template 350 can be selected to correspond with the desired shape of the air-laid fibrous article 100 in the MD-CD plane of the air-laid fibrous article 100 or the proper shape for further downstream processing. The term downstream can be understood as the direction of processing from the start of manufacturing the absorbent article towards the end of manufacturing. The term upstream can be understood as the direction in processing opposite downstream.

Figure 3:
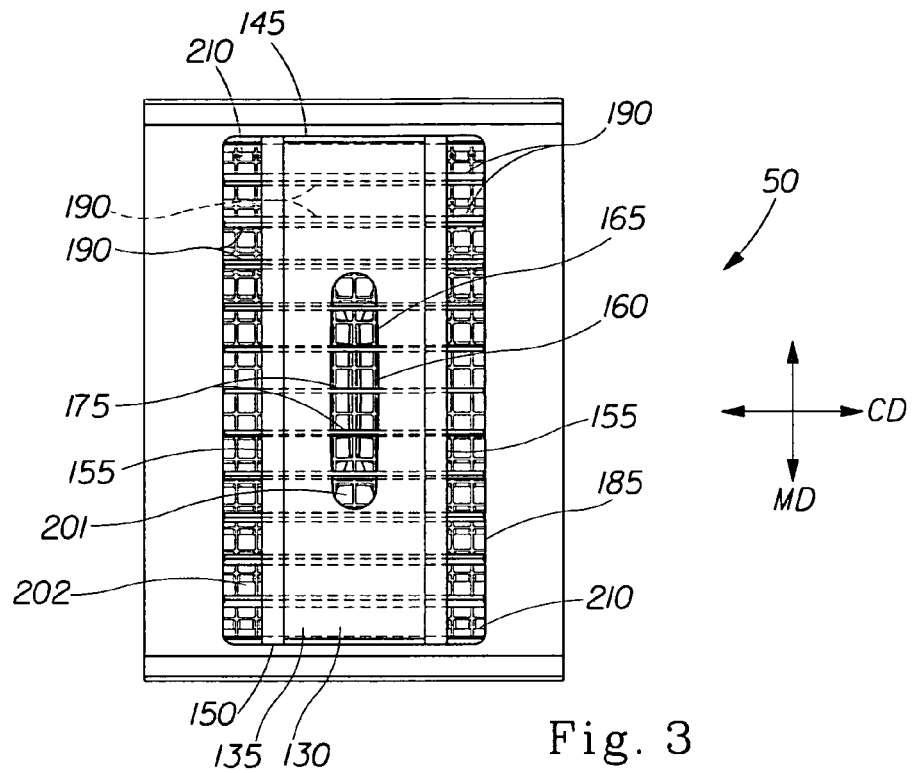
FIG. 3 is a bottom view of a core pocket.

A plan view of one embodiment of core pocket 50 in which the interior facing surface 135 of the shield 130 is presented to the viewer is shown in FIG. 3. As shown in FIG. 3, the core pocket 50 comprises a pair of edge openings 210. The edge openings 210 extend along each side of the shield 130 in the machine direction and extend laterally in the cross direction beyond the shield lateral side edges 155. The edge openings 210 are defined by the spaces between the shield lateral side edges 155 and the edges of the edge forming chamber 185. The edge forming chamber 185 can be in air-flow communication with the edge openings 210. The edge openings 210 can extend from the shield first end 145 to the shield second end 150. The shield 130 can be generally rectangular. Other shapes of the shield 130 are also possible.

By way of example, and not to be limiting, each edge opening 210 can have a width in the cross direction between about 10 mm and about 60 mm.

The core pocket 50 can be configured such that different air pressures can be applied to the central foraminous forming surface 180 and the edge foraminous forming surface 195. Ambient air pressure, positive air pressure, and negative air pressure can be useful in forming air-laid fibrous articles. In describing positive, ambient and negative air pressures, as used herein, the origin dividing positive pressure and negative pressure is atmospheric pressure (approximately 101.325 kPa), with positive pressures defined as being greater than one atmosphere, ambient pressure being atmospheric pressure, and negative pressures being less than one atmosphere. Particular magnitudes of pressure reported herein are absolute pressures.

In the embodiment shown in FIG. 3, air pressure applied to the central opening 160 can be transmitted through the central opening 160, between the central lateral baffles 175 and into the central forming chamber 165. Air pressure in the central forming chamber 165 can be applied to the central foraminous forming surface 180. If a central support mesh 201 is present, air pressure can be transmitted though the central support mesh 201 to the central foraminous forming surface 180. The wall or walls of the central forming chamber 165 can be made of material impervious to air-flow and joined to one another by seals, seams, welds, or connections that are also impervious to air-flow. Thus, the central forming chamber 165 and edge forming chamber 185 can be isolated from one another in that the air pressure in the central forming chamber 165 can be different than the air pressure in the edge forming chamber 185 and air-flow between the central forming chamber 165 and the edge forming chamber 185 can be small enough to be negligible or even nonexistent. Thus, the edge foraminous forming surface 195 can have a pressure applied thereto that is independent of the pressure applied to the central foraminous forming surface 180 and the pressures applied to the edge foraminous forming surface 195 and the central foraminous forming surface 180 can be independently controlled.

In the embodiment shown in FIG. 3, air pressure applied to the edge openings 210 can be transmitted through the edge openings 210, between the edge lateral baffles 190 into the edge forming chamber 185. With or without the edge lateral baffles, air pressure applied to the edge openings 210 can be transmitted throughout the edge forming chamber 185 such that the pressure applied to the edge openings 210 is also applied to the portions of the edge forming chamber 185 overlying the shield 130. Thus, an "island" of one pressure can be applied to the central foraminous forming surface 180 that is surrounded by a "ring" of another pressure. In effect, pressure applied to the edge forming chamber 185 is bridged across the shield 130.

Air pressure in the edge forming chamber 185 can be applied to the edge foraminous forming surface 195. If edge support mesh 202 is present, air pressure can be transmitted through the edge support mesh 202 to the edge foraminous forming surface 195.

Figure 4:
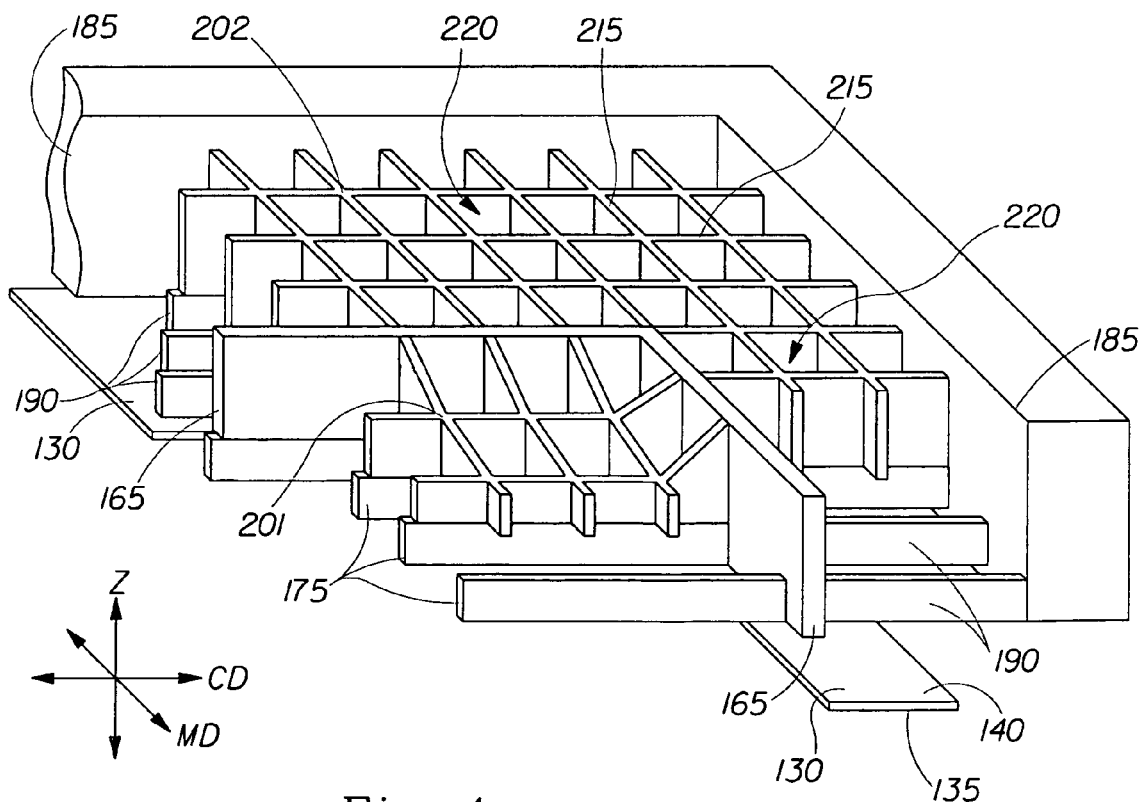
FIG. 4 is a cutaway view of a core pocket with the central support mesh and edge support mesh exposed.

If a central support mesh 201 is present, the central support mesh 201 can be joined to the edges of the central forming chamber 165, as shown in FIG. 4. The central support mesh 201 can provide support to the central foraminous forming surface 180 by distributing load applied to the central foraminous forming surface 180 to the boundaries of the central forming chamber 165 and/or to the central lateral baffles 175, which can reduce deformation of the central foraminous forming surface 180. As shown in FIG. 4, the central support mesh 201 can be inset into the central forming chamber 165 such that central support mesh 201 is about flush with the exterior edge of the central forming chamber 165 that is oriented away from the exterior facing surface 140 of shield 130.

Similarly, if edge support mesh 202 is present, the edge support mesh 202 can be joined to the boundaries of the edge forming chamber 185 and the boundaries of the central forming chamber 165. The edge support mesh 202 can provide support to the edge foraminous forming surface 195 in the same manner as the central support mesh 201. The edge support mesh 202 can be inset into the edge forming chamber 185 such that edge support mesh 202 is about flush with the exterior edge of the edge forming chamber 185 that is oriented away from the exterior facing surface 140 of shield 130. In this arrangement, the central forming chamber 165 can be described as projecting through the central support mesh 201 and the edge support mesh 202. In this arrangement, air flow between the central forming chamber 165 and the edge forming chamber 185 can be small enough to be negligible or even non-existent and the air pressure in the central forming chamber 165 can be different from the air pressure in the edge forming chamber 185. Without being bound by theory, it is thought that by delivering different pressures to the edge forming chamber 185 and central forming chamber 165, the amount of scarfing needed to form a fibrous article having one surface that is contoured in the z-direction and another surface that is flat can be reduced.

The central support mesh 201 can extend between the central foraminous forming surface 180 and the central lateral baffles 175 and can be in contact with the central foraminous forming surface 180 and the central lateral baffles 175, if present. In this configuration, the central support mesh 201, which can be a structure having a plurality of open spaces, can fill all the space between the central foraminous forming surface 180 and the central lateral baffles 175 if present.

The edge support mesh 202 can extend between the edge foraminous forming surface 195 and the edge lateral baffles 190 and can be in contact with both the edge foraminous forming surface 195 and the edge lateral baffles 190, if present. In this configuration, the edge support mesh 202, which can be a structure having a plurality of open spaces, can fill all the space between the edge foraminous forming surface 195 and the edge lateral baffles 190 if present.

The central support mesh 201 and edge support mesh 202 can be comprised of stainless steel, titanium, or other material suitable for use in high speed manufacturing operations. Support mesh can be a product described as honeycomb disclosed in WO2001042549A1, filed Dec. 8, 2000 and WO2000029656A1, filed Nov. 17, 1999, or WO2001098574A2, filed Jun. 19, 2001. The central support mesh 201 and edge support mesh 202 can have a high percent open area permitting air flow without significant resistance. The central support mesh 201 and edge support mesh 202 can have a plurality of open spaces. The central support mesh 201 and the edge support mesh 202 can be a web of sheet metal comprised of strips of corrugated sheet metal joined to one another at the bending axes of the corrugations.

As shown in FIG. 4, central support mesh 201 and edge support mesh 202 can be comprised of mesh walls 215 and mesh cells 220. Portions of the mesh walls 215 can be coordinated to be in alignment with the edges of central lateral baffles 175, thereby substantially preventing movement of air in the machine direction of central forming chamber 165. Portions of the mesh walls 215 can be coordinated to be in alignment with and sealed to the central lateral baffles 175, thereby substantially preventing movement of air in the machine direction of central forming chamber 165.

The edge support mesh 202 can be configured with respect to the edge foraminous forming surface 195 and the edge lateral baffles 190 in the same manner as the central support mesh 201 can be configured with respect to the central foraminous forming surface 180 and the central lateral baffles 175. Portions of the mesh walls 215 can be coordinated to be in alignment with the edges of edge lateral baffles 190, thereby substantially preventing movement of air in the machine direction of edge forming chamber 185. Portions of the mesh walls 215 can be coordinated to be in alignment with and sealed to the edge lateral baffles 190, thereby substantially preventing movement of air in the machine direction of edge forming chamber 185.

The mesh walls of the central support mesh 201 and the edge support mesh 202 need not be in alignment with or sealed to the central lateral baffles 175 and edge lateral baffles 190. In general, small mesh cells 220 can sufficiently resist air flow in the machine direction of the core pocket. By way of example, and not to be limiting, mesh cells 220 having approximately rectangular openings about 13 mm by about 5 mm, in a staggered relationship, such as a running or stretcher bond brick pattern, can be used to sufficiently reduce air flow in the machine direction of the core pocket 50. By way of example, and not to be limiting, the central support mesh 201 and edge support mesh 202 can be comprised of material having a thickness of about 0.2 mm. Without being bound by theory, it is thought that the tortuous pathway for air flow through the spaces between the central support mesh 201 and central lateral baffles 175 and the spaces between the edge support mesh 202 and the edge lateral baffles 190 can offer sufficient resistance to air flow in the machine direction of the core pocket 50.

Figure 5:
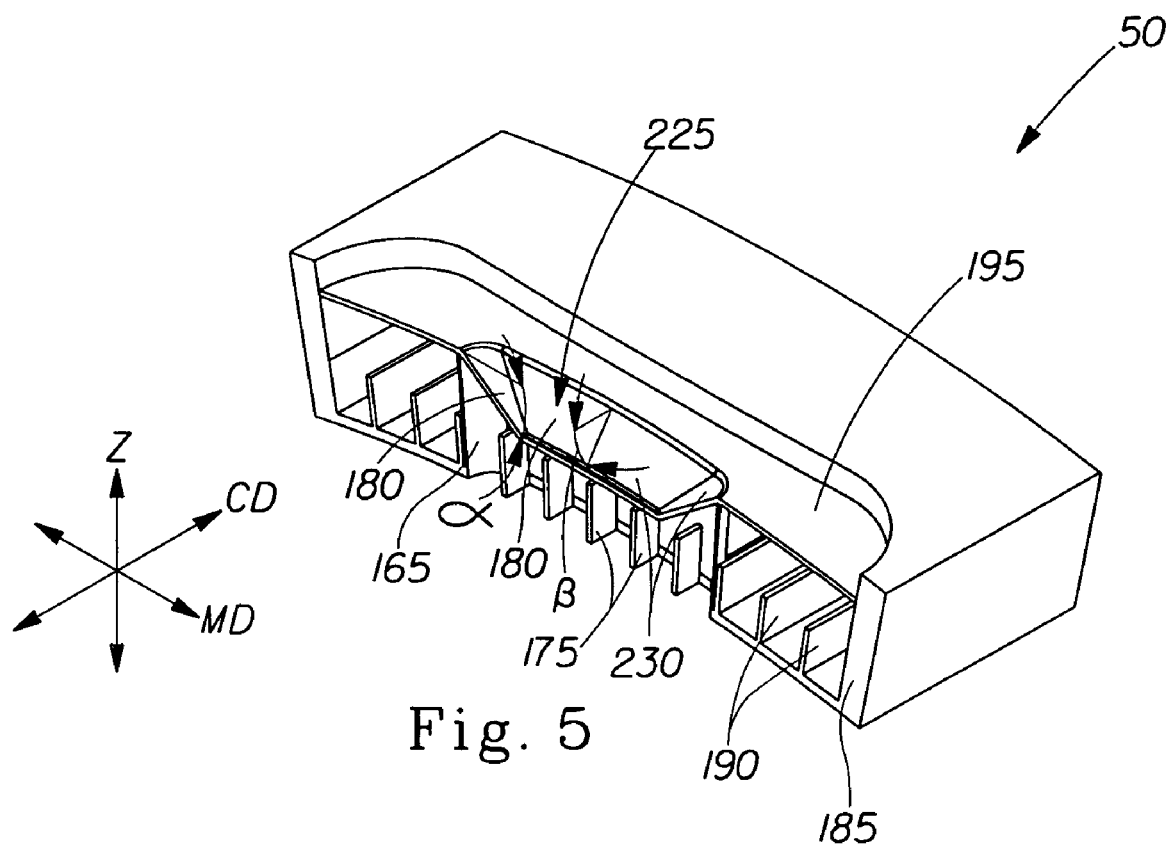
FIG. 5 is a cutaway view of one embodiment of the core pocket, as indicated by Section 5-5.

In one embodiment of the core pocket 50, central foraminous forming surface 180 can have a recessed portion relative to the edge foraminous forming surface 195. Non-limiting examples for the shape of the recess can include a frustum, a frustum having an oval shaped base, a frustum having an irregularly shaped base and top, and a pyramidal frustum. As shown in FIG. 5, the central foraminous forming surface 180 and edge foraminous forming surface 195 can be considered to a have a machine direction MD and a cross direction CD. The recessed portion 225 can be generally characterized by the angles formed by the recess in the machine direction and cross direction. The angle of the recess in the machine direction α can be between about 0° and about 90°, with 0° corresponding to an arrangement in which the central foraminous forming surface 180 is not recessed relative to the edge foraminous forming surface 195. The angle of the recess in the machine direction α can be between about 1° and about 45°. The angle of the recess in the cross direction β can be between about 0° and about 90°, with 0° corresponding to an arrangement in which the central foraminous forming surface 180 is not recessed relative to the edge foraminous forming surface 195. The angle of the recess in the cross direction β can be between about 1° and about 70°. The specific ranges for angles α and β are provided by way of example and not to be limiting. The angles α and β can be the same or different and the angle on one side of the recess can be different from the angle on the opposing side. The recess walls 230 can be straight or curved, combinations of straight sections, combinations of curved sections, or combinations of straight and curved sections. The configurations for the recessed portion 225 described herein are by way of example only and not to be limiting as other configurations are possible. The central foraminous forming surface 180 and the edge foraminous forming surface 195 can be in plane with one another so as to be considered flat with respect to one another.

Figure 6:
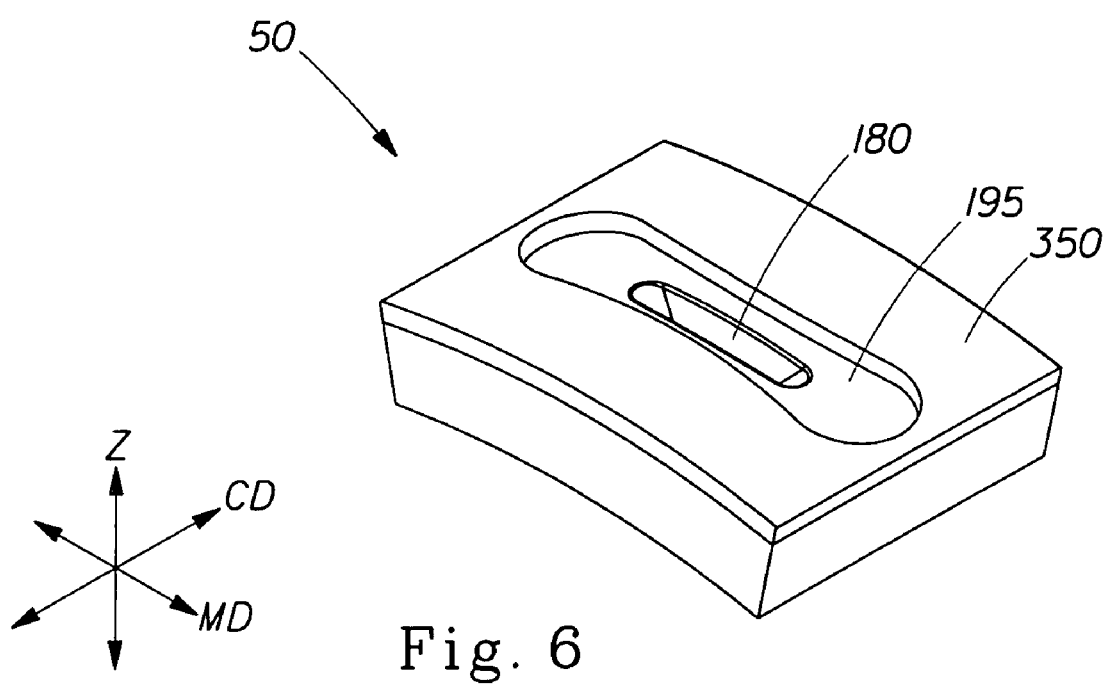
FIG. 6 is a perspective view of one embodiment of the core pocket.

By way of example, and not to be limiting, the edge foraminous forming surface 195 and the central foraminous forming surface 180, upon which fibers are deposited, can have the shape of a core of a sanitary napkin, diaper, incontinent pad, or other absorbent article designed to be worn in the crotch of the wearer. A perspective cut-away view illustrating an edge foraminous forming surface 195 and a central foraminous forming surface 180, upon which fibers are deposited, having the shape of a core for sanitary napkin is shown in FIG. 5. To provide for a well defined periphery and thickness of the air-laid fibrous article 100, the central foraminous forming surface 180 and the edge foraminous forming surface 195 can be recessed relative to the boundaries of the edge forming chamber 185, as shown in FIG. 5, or recessed relative to a peripheral edge template 350, as shown in FIG. 6.

As discussed previously, the core pocket 50 can optionally comprise a peripheral edge template 350 that can provide for a well defined periphery and thickness of the air-laid fibrous article 100. By overlaying a peripheral edge template 350 over the foraminous forming surfaces, the foraminous forming surfaces can be recessed relative to the exterior facing surface of the core pocket 50 which is the side of the core pocket 50 oriented away from the shield 130.

By way of example, and not to be limiting, the peripheral edge template 350 can have the shape of a core of a sanitary napkin, diaper, incontinent pad, or other absorbent article designed to be worn in the crotch of the wearer.

Figure 7:
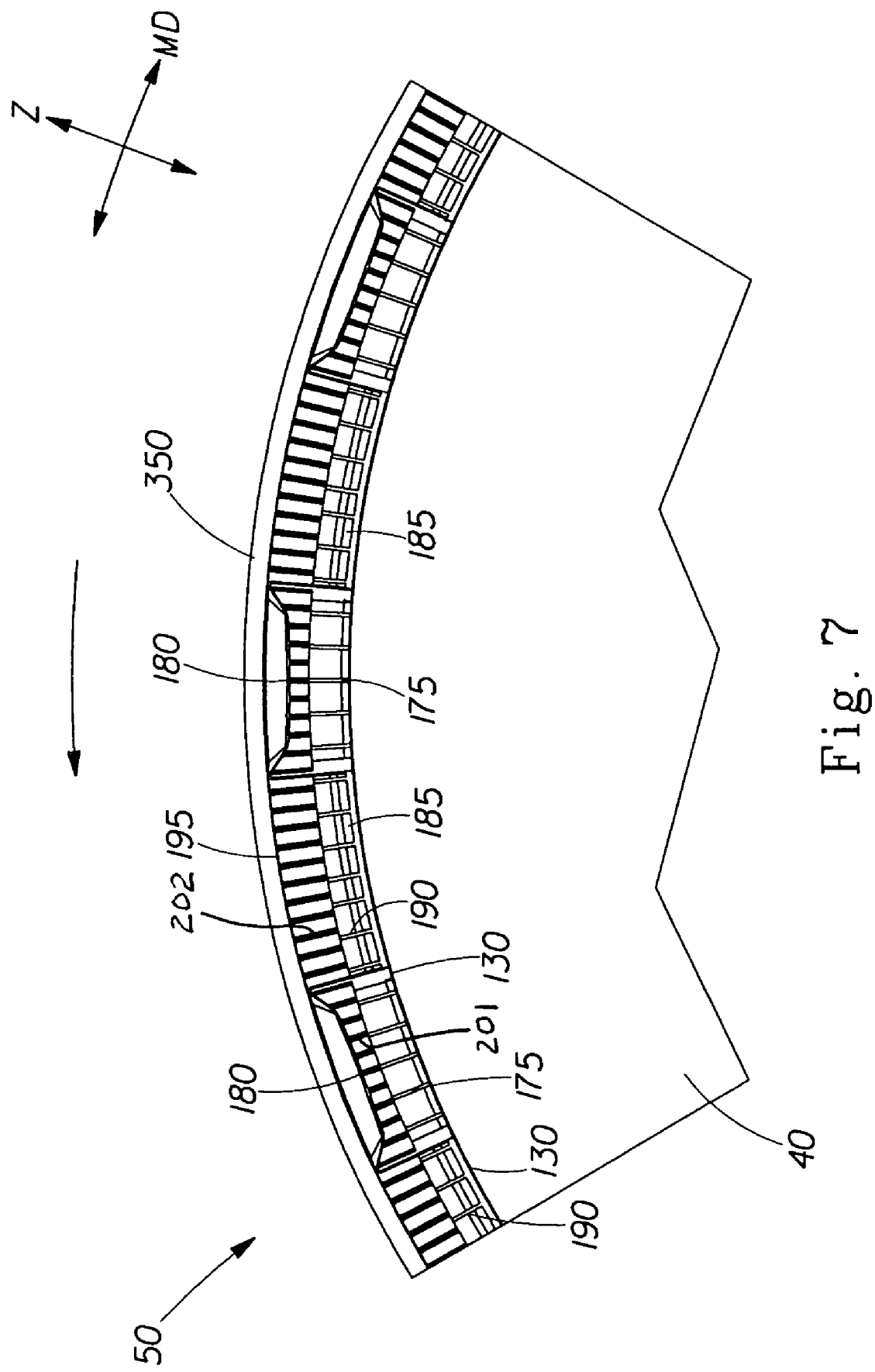
FIG. 7 is a cross sectional view of a core pocket comprising a plurality of central forming chambers in an edge forming chamber, the core pocket being mounted on a deposition drum (viewed from the opposite side as the view provided in FIG. 1).

The core pocket 50 can comprise one or more central forming chambers 165 disposed in a single edge forming chamber 185, as shown in FIG. 7. FIG. 7 is a cross sectional view of a core pocket 50 mounted on deposition drum 40 as viewed from the opposite side as the view provided in FIG. 1. In the embodiment shown in FIG. 7, the core pocket 50 has a plurality of central forming chambers 165 within a single edge forming chamber 185. In this configuration, a web of air-laid fibrous material in which a plurality of zones of material deposited above the central forming chambers can be formed with the apparatus 10. A single edge forming chamber 185 can extend circumferentially about deposition drum 40.

In apparatus 10 in which the core pockets 50 are disposed in a circumferential relationship about the periphery of deposition drum 40, all of the components of the core pocket 50 can have an arcuate shape in the machine direction. By way of example, and not to be limiting, a core pocket 50 having an arcuate shape in the machine direction can have a length as measured in the machine direction between about 0.15 and about 0.55 radians. By way of example, and not to be limiting, the central opening 160 for a core pocket 50 having an arcuate shape in the machine direction can have a length as measured in the machine direction between about 0.1 and about 0.4 radians.

In apparatus 10, in which the core pockets are not disposed about the periphery of a deposition drum 40 but travel in a flat plane as air-laid fibrous articles 100 are formed, the core pocket 50, and the components thereof, can have a flat shape in the machine direction.

An embodiment of apparatus 10 further comprising an air-distribution manifold 60 operatively related to the core pocket 50 is shown in FIG. 1. By operatively related it is meant that the air-distribution manifold 60 is positioned such that the core pocket 50 can slide along the air-distribution manifold 60. In one embodiment, the air-distribution manifold 60 can have a curved air-distribution surface. Air-distribution manifold 60 can be stationary. In the embodiment shown in FIG. 1, the core pocket 50 can slide along the air-distribution manifold 60 as the deposition drum 40 rotates. In this embodiment, the core pocket 50 can be disposed in a circumferential relationship about the periphery of deposition drum 40. The shield 130, central forming chamber 165, and edge forming chamber 185 can have an arcuate shape in the machine direction that generally conforms to the curved peripheral surface of the air-distribution manifold 60. The radius of curvature of the shield 130, central forming chamber 165, and edge forming chamber 185 can be about the same or slightly greater than the curvature of the air-distribution surface of the air-distribution manifold 60. Furthermore, by operatively related, it is meant that the air-distribution manifold 60 can be in air-flow communication with one or more core pockets 50 as the deposition drum 40 rotates about the air-distribution manifold 60 such that controlled magnitudes of air pressure can be applied to portions of the core pocket 50. For example, the air pressure applied by the air-distribution manifold 60 to the central forming chamber 165 can differ from the air pressure applied to the edge forming chamber 185.

Figure 8:
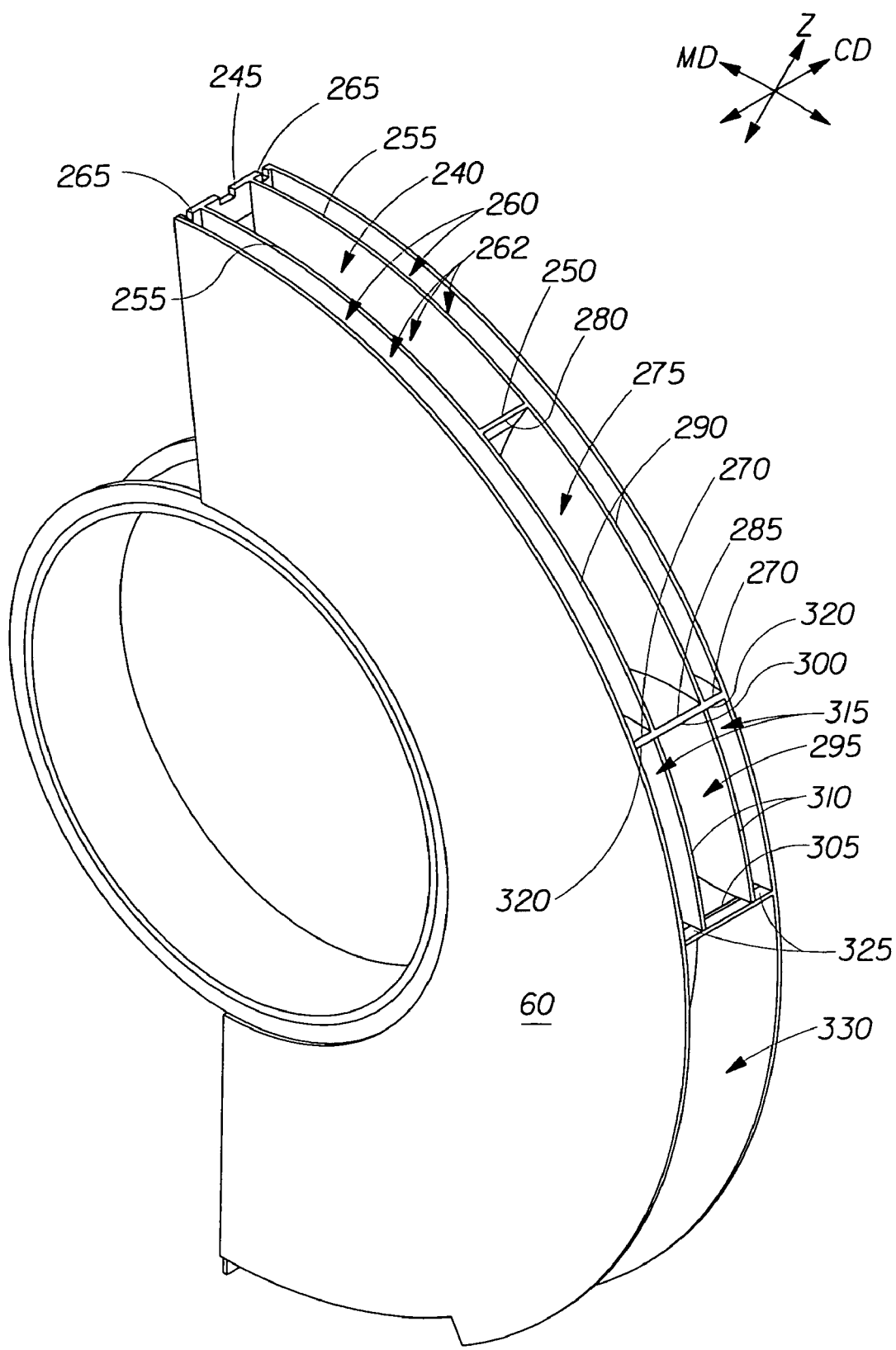
FIG. 8 is a perspective view of one embodiment of an air-distribution manifold.

As shown in FIG. 8, the air-distribution manifold 60 can comprise a central zone 240. The central zone 240 can have a central zone first end 245 and a central zone second end 250 opposing the central zone first end 245. The central zone 240 can have a pair of opposing central zone lateral side edges 255 extending from the central zone first end 245 to the central zone second end 250. The air-distribution manifold 60 can further comprise a pair of edge zones 260. The edge zones 260 can be adjacent to the central zone lateral side edges 255.

Without being bound by theory it is thought that by having the edge zones 260 adjacent the central zone lateral side edges 255 and forming the air-laid fibrous article 100 from a single stream of air-entrained fibers that certain beneficial results can occur. For instance, it is thought that air-laid fibrous articles 100 formed in this manner have a more coherent mechanical structure than if one stream of air-entrained fibers 12 is used to deposit fibers on the edge foraminous forming surface 195 and another stream of air-entrained fibers is used to deposit fibers on the central foraminous forming surface 180.

In describing the central zone 240 as having a central zone first end 245, the central zone first end 245 is the end of the central zone 240 which the core pocket 50 first encounters as the core pocket 50 reaches the location in the apparatus where air-entrained fibers are directed to the core pocket 50. The central zone second end 250 is the end of the central zone 240 which the core pocket 50 encounters as the core pocket 50 slides along the air-distribution manifold 60 after the core pocket 50 has passed the central zone first end 245.

The central zone 240 and the edge zones 260 are not in air-flow communication with one another as the core pocket 50 slides along the zones of the air-distribution manifold 60. That is, the air pressure in the central zone 240 can be maintained at a pressure that differs from the air pressure in the edge zones 260 and the air-flow between the central zone 240 and the edge zones 260 can be small enough to be to be negligible. The air pressure in the central zone 240 and edge zones 260 can be controlled independently. To reduce the amount of air-flow between the central zone 240 and the edge zones 260 when the core pocket 50 is overlying these zones, a sealing material, such as felt, can be affixed along the boundaries between the central zone 240 and the edge zones 260. To further reduce the amount of air-flow between the central zone 240 and the edge zones 260 when the core pocket 50 is overlying these zones, a sealing material, such as Multifill Bearing Tape having a width of about 1 cm and a thickness of about 0.8 mm supplied by Garlock Bearings, LLC, can be affixed to the interior facing surface 135 of the shield 130 such that the sealing material is approximately coincident with the boundaries between the central zone 240 and the edge zones 260 of the air-distribution manifold 60 and aligned in the machine direction of the core pocket 50.

As shown in FIG. 8, each edge zone 260 can have an edge zone first end 265. The edge zone first end 265 can be aligned with the central zone first end 245. The edge zone first end 265 does not have to be aligned with the central zone first end 245. Each edge zone 260 can further have an edge zone second end 270 opposing the edge zone first end 265. The edge zone second end 270 can be aligned with the central zone second end 250. The edge zone second end 270 does not have to be aligned with the central zone second end 250. Furthermore, the edge zones 260 need not have the same geometry as one another. Each edge zone 260 need not have the same length, as measured in the machine direction, as another edge zone 260.

The air-distribution manifold 60 can further comprise a central recycle zone 275, as shown in FIG. 8. The central recycle zone 275 can have a central recycle zone first end 280, a central recycle zone second end 285 opposing the central recycle zone first end 280, and a pair of opposing central recycle zone lateral side edges 290 extending from the central recycle zone first end 280 to the central recycle zone second end 285. The central recycle zone first end 280 can be adjacent the central zone second end 250, as shown in FIG. 8. The central recycle zone first end 280 can be located some distance away from the central zone second end 250. As in the embodiment shown in FIG. 8, the edge zone second ends 270 can be aligned with the central recycle zone second end 285. The central recycle zone 275 can have a width that is the same as the width of the central zone 240.

The air-distribution manifold 60 can further comprise a central scarfing zone 295. The central scarfing zone 295 can have a central scarfing zone first end 300 and a central scarfing zone second end 305 opposing the central scarfing zone first end 300. The central scarfing zone 295 also can have a pair of opposing central scarfing zone lateral side edges 310, each of which can extend from the central scarfing zone first end 300 to the central scarfing zone second end 305. The central scarfing zone first end 300 can be adjacent the central recycle zone second end 285. The central scarfing zone 295 can have a width that is the same as the width of the central zone 240.

As shown in FIG. 8, the air-distribution manifold 60 can further comprise a pair of edge scarfing zones 315 adjacent the central scarfing zone lateral side edges 310. Each edge scarfing zone 315 has an edge scarfing zone first end 320 and an edge scarfing zone second end 325 opposing the edge scarfing zone first end 320. The edge scarfing zone first end 320 can be aligned with the central scarfing zone first end 300. The edge scarfing zone second end 325 can be aligned with the central scarfing zone second end 305. The pressure applied at the central scarfing zone 295 can be about 12 kPa. The pressure applied at the central scarfing zone 295 can be between about 2 kPa and about 20 kPa. These pressures are provided by way of example and are not to be limiting. The edge scarfing zones 315 can each have the same width as edge zones 260.

The air-distribution manifold 60 can also comprise a hold down zone 330. The hold down zone 330 can be disposed adjacent the central zone second end 250, if central scarfing zone 295 and central recycles zone 275 are not present. The hold down zone 330 can be disposed adjacent the central recycle zone second end 285. As shown in FIG. 8, the hold down zone 330 can be disposed adjacent the central scarfing zone 295. The hold down zone 330 can be disposed adjacent the central scarfing zone second end 305. The pressure applied at the hold down zone 330 can be about 4 kPa. The pressure applied at the hold down zone 330 can be between about 1 kPa and about 10 kPa. These pressures are provided by way of example and not to be limiting.

The central zone 240 has a central zone width in the cross direction defined by the shortest distance between the central zone lateral side edges 255. The central zone width can be between about 15 mm and about 50 mm. The central zone 240 can have a width of about 31 mm. The length of the central zone 240, as measured in the machine direction can be about 195 mm. Each edge zone 260 also has an edge zone width in the cross direction. The edge zone width can be between about 5 mm and bout 40 mm. The edge zone width can be about 12 mm. The length of each edge zone 260, as measured in the machine direction, can be about 363.5 mm. The central recycle zone width can be about the same as the central zone width. The central scarfing zone 295 can have a central scarfing zone width defined by the shortest distance between the central scarfing zone lateral side edges 310. The central scarfing zone width can be about the same as the central zone width. Each edge scarfing zone width can be about the same as each edge zone width. The edge scarfing zone length, as measured in the machine direction, can be about 104.5 mm. The hold down zone 330 has a hold down zone width in the cross direction. The hold down zone width can be between about 30 mm and about 90 mm. The hold down zone width can be about 60 mm. The hold down zone width can be about the same as the sum of the central zone width and each edge zone width. The length of the hold down zone, as measured in the machine direction, can be about 104.5 mm. The central zone widths, edge zone widths, central recycle zone width, central scarfing zone width, edge scarfing zone width, and hold down zone width provided herein are by way of example and not to be limiting given that these dimensions are ultimately governed by the desired geometry of air-laid fibrous article 100, the dimensions of the core pocket 50, and the geometry of the air-distribution manifold 60. For an air-distribution manifold 60 having a curved air-distribution surface 262, the lengths reported are lengths about the circumference of the air-distribution manifold 60.

As with the boundary between the central zone 240 and edge zone 260, sealing materials can be applied between the boundaries of the different zones of the air-distribution manifold 60.

The central zone 240 is in air-flow communication with a source of air pressure. The air pressure in the central zone can be negative. Some people skilled in the art refer to negative pressure as vacuum or vacuum pressure. Similarly, each edge zone 260 is in air-flow communication with a source of air pressure. The air-distribution manifold 60 can be operatively related to one or more core pockets 50 such that as a core pocket 50 slides along the air-distribution manifold 60, the central zone 240 of the air-distribution manifold 60 can be in air-flow communication with the central opening 160 in the shield 130. Furthermore, the air-distribution manifold 60 can be operatively related to one or more core pockets 50 such that as the core pocket 50 slides along the air-distribution manifold 60, the edge zones 260 can be in air-flow communication with the edge openings 210 of the core pocket 50.

The pressure applied at the edge zones 260 can differ from the pressure applied at the central zone 240. The pressure applied at the central zone 240 and the edge zones 260 can be between about 6.7 kPa and about 16 kPa. The pressure applied at the central zone 240 and the edge zones 260 can be between about 2 kPa and about 20 kPa. These pressures are by way of example only and are not to be limiting, as other pressures can be applied at the central zone 240 and edge zones 260 with the result that air-laid fibrous articles having different properties can be formed.

The air-distribution manifold 60 illustrated in FIG. 8 has a curved air-distribution surface 262. The air-distribution surface 262 is the portion of the air-distribution manifold 60 facing the core pocket 50 as the core pocket 50 slides over the air-distribution manifold 60. The shield 130, central forming chamber 165, and edge forming chamber 185 can have an arcuate shape in the machine direction that generally conforms to the air-distribution surface 262. The air-distribution manifold 60 can have a flat air-distribution surface 262.

For an air-distribution manifold 60 having a curved air-distribution surface 262, the central zone 240 can extend between about 0.5 radians and about 0.7 radians. If present, the edge zones 260 can extend between about 0.5 radians and about 1.4 radians. If present, the central recycle zone 275 can extend between about 0.5 and about 0.7 radians. If present, the central scarfing zone 295 and edge scarfing zones 315 can extend between about 0.2 radians and about 0.4 radians. The hold down zone 330, if present, can extend between about 0.5 radians and about 0.8 radians. The dimensions for the central zone 240, edge zones 260, central recycle zone 275, central scarfing zone 295, edge scarfing zones 315, and hold down zone 330 are provided by way of example and not to be limiting. Other dimensions for the central zone 240, edge zones 260, central recycle zone 275, central scarfing zone 295, edge scarfing zones 315, and hold down zone 330 are possible.

Figure 9:
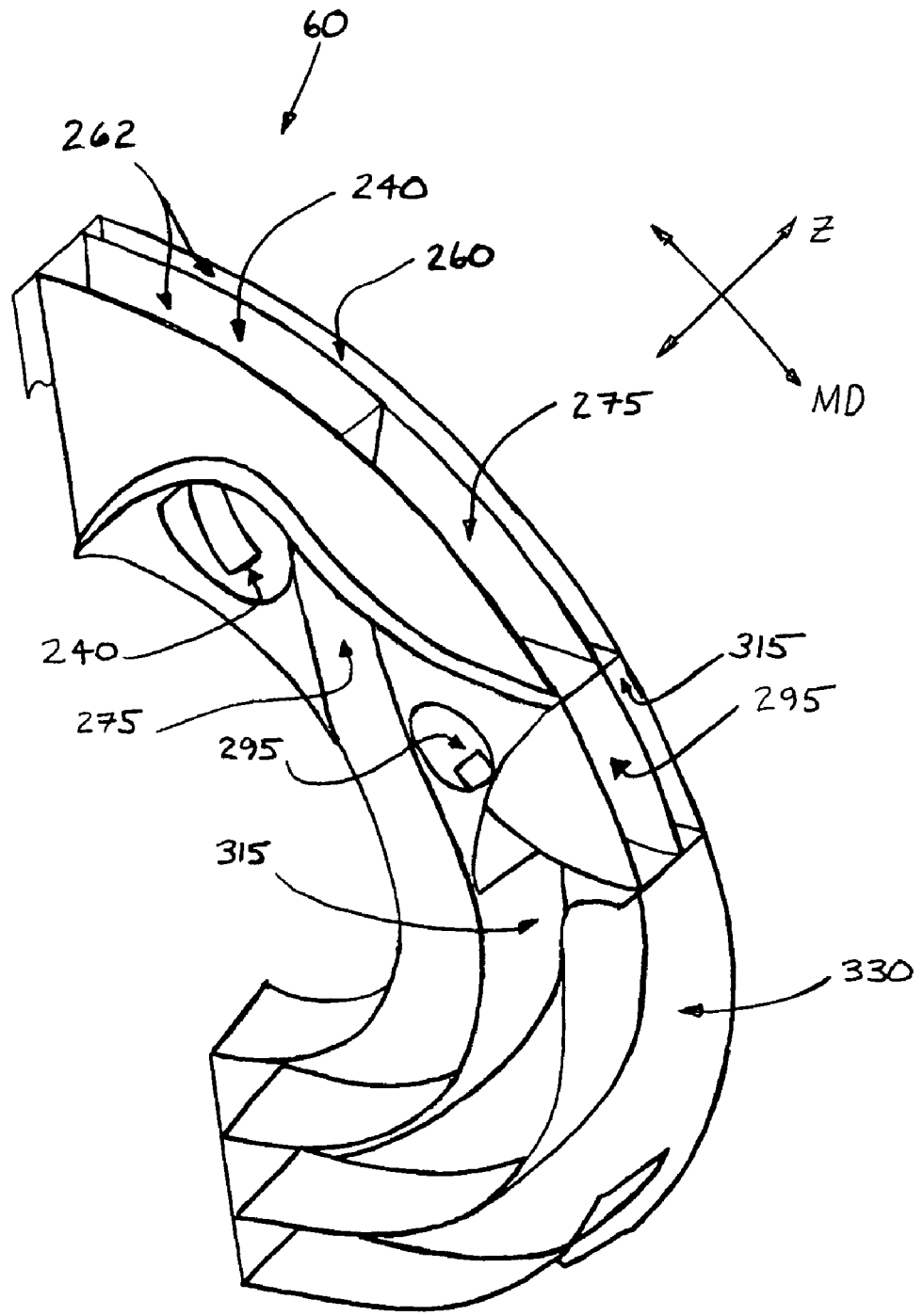
FIG. 9 is a cutaway view of one embodiment of an air-distribution manifold.

A cutaway view of one embodiment of the air-distribution manifold 60 is shown in FIG. 9. As shown in FIG. 9, air pressure can be conducted or conveyed through ducts within the air-distribution manifold 60 to various portions of the air-distribution surface 262. As known by those skilled in the art, there are many possible designs that are suitable for conducting pressures to different portions of an air-distribution manifold.

In one embodiment of apparatus 10 in which the air-distribution manifold 60 has a curved air-distribution surface 262, the core pocket 50 can slide along the air-distribution manifold at an angular velocity of between about 2 radians per second and about 10 radians per second. The core pocket 50 can slide along the air-distribution manifold at an angular velocity of about 7.2 radians per second. The range and particular values for angular velocity for the core pocket 50 are provided by way of example and not to be limiting as other values for the angular velocity of the core pocket 50 are possible.

Figure 10:
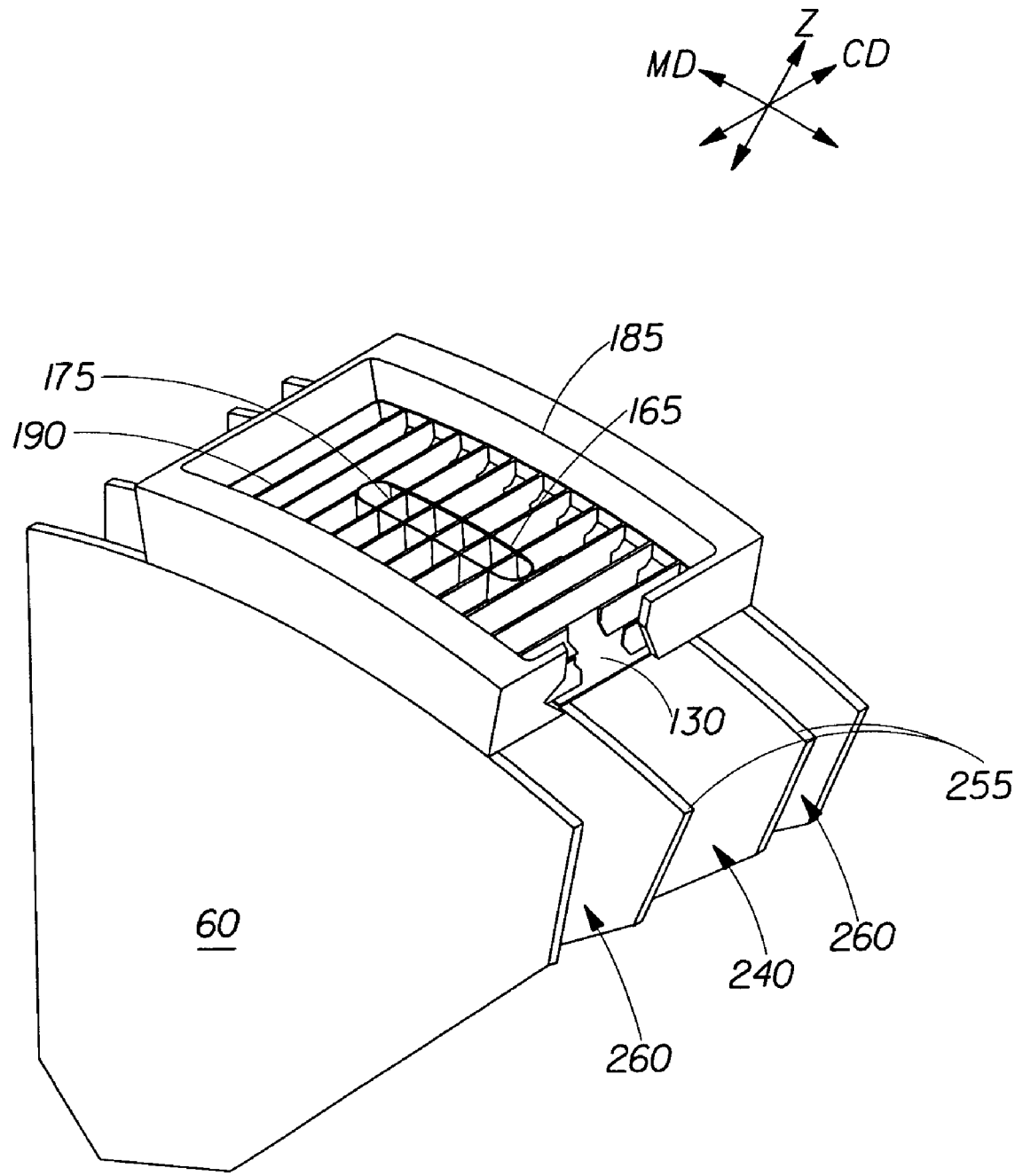
FIG. 10 is schematic of how components of the core pocket can be operatively related to the air-distribution manifold.

An illustration of one embodiment in which the air-distribution manifold 60 is in operative relationship with a portion of a core pocket 50 is shown in FIG. 10. The central zone 240, shield 130, and central opening 160 are sized and dimensioned so that air pressure in the central zone 240 can be transmitted to the central forming chamber 165, but not to the edge forming chamber 185. Similarly, each edge zone 260 of the air-distribution manifold 60 can be in air-flow communication with each edge opening 210 and thereby the edge forming chamber 185. Each edge zone 260 and each edge opening 210 is sized and dimensioned so that air pressure in the edge zones 260 is transmitted to the edge forming chamber 185, but not to the central forming chamber 165. By operatively relating the core pocket 50 and air-distribution manifold in this manner, the pressure applied to the central foraminous forming surface 180 can be independently controlled and differ from the pressure applied to the edge foraminous forming surface 195.

By applying different pressures to the central foraminous forming surface 180 and the edge foraminous forming surface 195, fibrous articles having a basis weight that varies in the machine direction and cross direction can be formed. For instance, if the central foraminous forming surface 180 is acted upon by a negative pressure, air-entrained fibers discharged from discharge chute 30 are drawn to the central foraminous forming surface. The velocity of air-entrained particles can be a function of the characteristics of the hammermill 20, the shape of the discharge chute 30, these features combining to affect the momentum of air-entrained fibers exiting the discharge chute in the absence of a negative pressure, and the pressure on either of the foraminous forming surfaces. If the pressure on the central foraminous forming surface 180 is less than the pressure on the edge foraminous forming surface 195, the momentum of the air-entrained fibers as they are directed towards the foraminous forming surfaces can be greater for fibers directed towards the central foraminous forming surface 180 than for fibers directed towards the edge foraminous forming surface 195. The basis weight of fibers deposited on the foraminous forming screens can be a function of the momentum of the fibers as the fibers are deposited, with higher basis weights occurring as a result of greater momentum. Thus, if the pressure on the central foraminous forming surface 180 is less than the pressure on the edge foraminous forming surface 195, the basis weight of the fibers deposited on the central foraminous forming surface 180 can be greater than the basis weight of the fibers deposited on the edge foraminous forming surface 195.

One skilled in the art can appreciate that different combinations of pressure acting on the foraminous forming surfaces can yield fibrous articles having different characteristics. For instance, if the difference in the pressure on the central foraminous forming surface 180 and the edge foraminous forming surface 195 is large, the contrast in basis weight of the fibrous article in the machine direction and cross direction can be large. If the pressure on the edge foraminous forming surface 195 is less than the pressure on the central foraminous forming surface 180, the basis weight of the fibrous article can be greater in portions of the fibrous article deposited on the edge foraminous forming surface 195 than in portions deposited on the central foraminous forming surface 180.

If the central foraminous forming surface 180 is recessed relative to the edge foraminous forming surface 195, the pressures applied to the central foraminous forming surface 180 and the edge foraminous forming surface 195 can be set at a magnitudes such that, as the core pocket moves towards the central scarfing zone 295 and edge scarfing zones 315, the level of the fibrous material overlying the edge foraminous forming surface 195 and the level of the fibrous material overlying the central foraminous forming surface 180 are about the same. Setting the pressures in this manner can reduce the amount of scarfing necessary to create an air-laid fibrous article 100 having a flat surface.

The pressure on either of the foraminous forming surfaces can be ambient. For fibers deposited on a foraminous forming surface upon which the pressure is ambient, the velocity of the fibers deposited on that surface can be substantially a function of the characteristics of the hammermill 20 and discharge chute 30.

In one embodiment, the pressure on the central foraminous forming surface 180 can be negative and the pressure on the edge foraminous forming surface 195 can be ambient. In this embodiment, negative pressure on the central foraminous forming surface 180 can draw air out from the edge zones 260, through the edge forming chamber 185, and through the edge foraminous forming surface 195 towards the central foraminous forming surface 180. In this configuration, air flow emanating from the edge foraminous forming surface 195 can assist in directing fibers 12 towards the central foraminous forming surface 180 and/or substantially reduce the amount of fibers 12 deposited on the edge foraminous forming surface 195. Negative pressure on the edge foraminous forming surface 195 and ambient pressure on the central foraminous forming surface 180 can employed similarly to assist in directing fibers 12 towards the edge foraminous forming surface 195 and/or substantially reducing the amount of fibers 12 deposited on the central foraminous forming surface 180.

The pressure on both the central foraminous forming surface 180 and the edge foraminous forming surface 195 can be negative. The pressure on the central foraminous forming surface 180 can be approximately the same as the pressure on the edge foraminous forming surface 195.

Central lateral baffles 175 can also be in slideable and sealable engagement with central zone 240. The central lateral baffles 175 divide the central forming chamber 165 into a plurality of central forming chamber lateral sections that are not in free air-flow communication with one another. Thus, the central lateral baffles 175 substantially reduce or prevent the movement of air in the machine direction through the central forming chamber 165.

Similarly, the edge lateral baffles 190 can be in slideable and sealable engagement with the edge zones 260. The edge lateral baffles 190 divide the edge forming chamber 185 into a plurality of edge forming chamber lateral sections that are not in free air-flow communication with one another. By this structure, movement of air in the machine direction through the edge forming chamber 185 can be substantially reduced or prevented.

Reducing movement of air in the machine direction of the core pocket may be desired because as the core pocket 50 slides along the air-distribution manifold 60, different portions of the core pocket 50 may be in air-flow communication with different zones of the air-distribution manifold 60. For instance, as the core pocket 50 moves in the machine direction during formation of the core, when the core pocket 50 is at a particular location, half of the edge openings 210 may be in air-flow communication with the edge zones 260 and the other half of the edge openings 210 may be in air-flow communication with the edge scarfing zones 315. Without edge lateral baffles 190, the air pressure acting on the edge forming chamber 185 would be approximately the resultant of the air pressures applied at the edge zones 260 and the edge scarfing zones 315. This would result in variations of the air pressure applied to portions of the edge foraminous forming surface 195 not corresponding to the location of the different portions of the edge foraminous forming surface 195 relative to the zones on an air-distribution manifold 60 comprising multiple zones. The net result on an air-laid fibrous article would be a gradual variation in the basis weight of the fibrous article in the machine direction, which may be undesirable. Central lateral baffles 175 can perform in the same manner.

Figure 11:
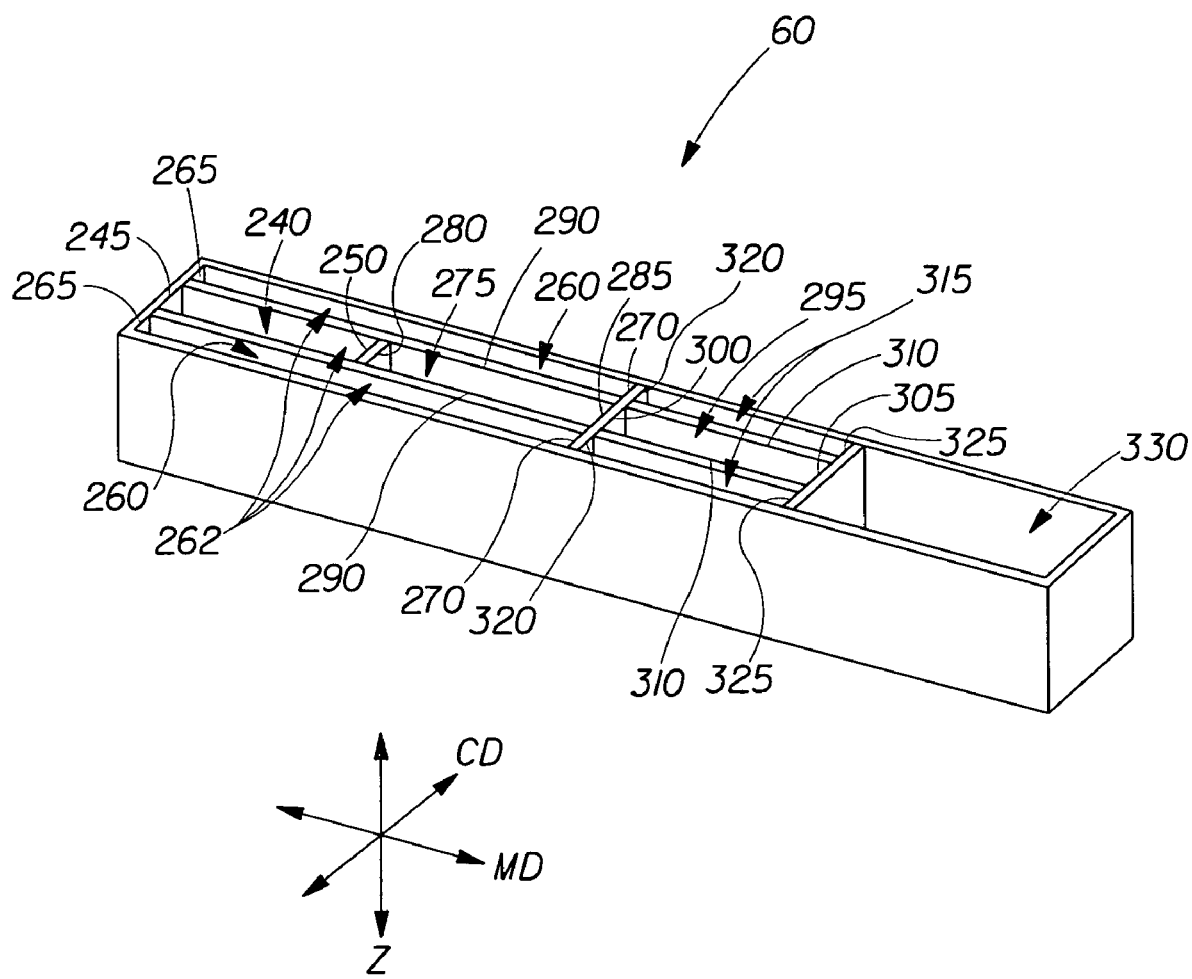
FIG. 11 is a schematic of an embodiment of the air-distribution manifold in which the air-distribution surface is flat.

An embodiment of an air-distribution manifold 60 having a flat air-distribution surface 262 is shown in FIG. 11. For an air-distribution manifold 60 having a flat air-distribution surface 262, the shield 130, central forming chamber 165, and edge forming chamber 185 also can have a flat shape that generally conforms to the flat air-distribution surface 262. An approach to operatively relating a core pocket to a flat air-distribution manifold is illustrated in U.S. Pat. No. 3,973,291 issued to Kolbach, Aug. 10, 1976.

The apparatus 10 can further comprise a scarfing roll 80 positioned in operative relationship with the core pocket 50.

The scarfing roll 80 can be positioned so that as the core pocket 50 slides along the air-distribution manifold 60 excess fibrous material deposited on the central foraminous forming surface 180 or the edge foraminous forming surface 195 can be scraped away. If excess fibrous material is deposited on the central foraminous forming surface 180 or the edge foraminous forming surface 195, the scarfing roll 80 contacts the outwardly facing free surface of the fibrous article. The scarfing roll 80 can be positioned such that scarfing roll 80 can contact the outwardly facing free surface of the fibrous article without contacting the core pocket 50.

Scarfing roll 80 can be a roll of blades rotating about a shaft, as is known in the art. The movement of the peripheral surface of scarfing roll 80 can remove uneven portions from the free surface of the air-laid fibrous article to produce a more uniform and level surface. The surface of the scarfing roll 80 can be adjusted to provide a desired contour along the scarfed surface of the fibrous article. The scarfing roll 80 can be disposed in a spaced adjacent relationship to the central foraminous forming surface 180 and the edge foraminous forming surface 195 as these surfaces move past the scarfing roll 80.

Scarfing roll 80 can rotate in a direction such that the peripheral surface of the scarfing roll 80 moves counter to the direction the fibrous article moves by the scarfing roll 80.

Figure 12:
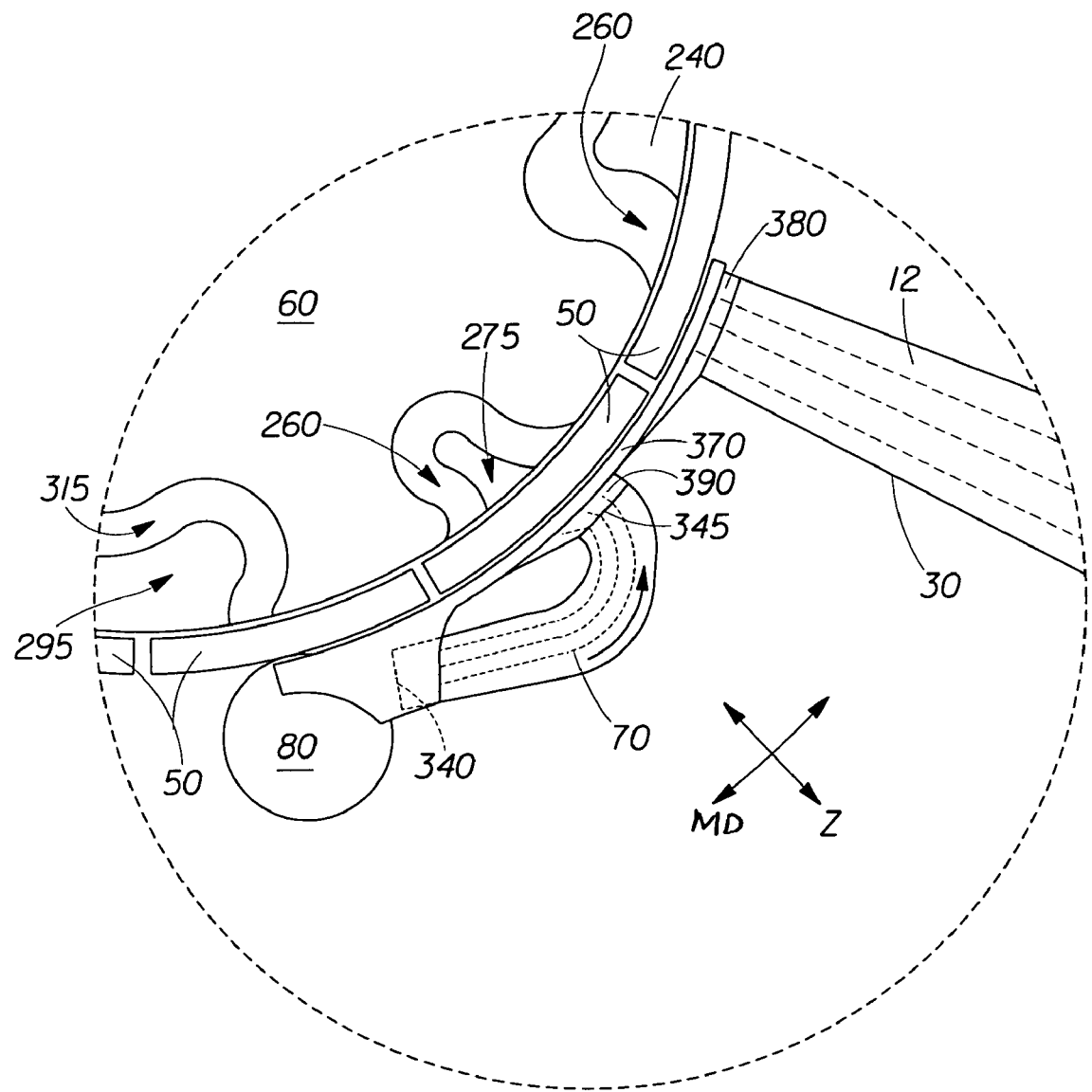
FIG. 12 is a cutaway view of apparatus 10, as indicated by Cutaway 12.

The apparatus 10 can further comprise a recycle duct 70. As shown in FIG. 12, the recycle duct 70 can have a recycle duct entrance 340 and a recycle duct exit 345. The recycle duct entrance 340 can be positioned in operative relationship with the scarfing roll 80. The recycle duct exit 345 can be positioned in operative relationship with the central recycle zone 275 and adjacent edge zones 260 of the air-distribution manifold 60, if present. The recycle duct exit 345 can be connected to a recycle distribution chamber 390. The recycle distribution chamber 390 can be positioned in operative relationship with the central recycle zone 275 and edge zones 260 adjacent the central recycle zone 275 of the air-distribution manifold 60 as the core pocket 50 passes between the air-distribution manifold 60 and the recycle duct exit 345. The recycle distribution chamber 390 can provide space in which the fibers 12 passing through the recycle duct 70 can be redistributed over the core pocket 50 when the core pocket 50 is in air-flow communication with the central recycle zone 275 and the edge zones 260 adjacent the central recycle zone 275. A portion of the recycled loose air-entrained fibers 12 discharged in the recycle distribution chamber 390 can be redeposited on the central foraminous forming surface 180 and another portion of the recycled loose air-entrained fibers 12 discharged in the recycle distribution chamber 390 can be redeposited on the edge foraminous forming surface 195.

Recycle duct 70 can be a tube of any shape that can convey air-entrained fibrous material. Recycle duct 70 can be a tube having a cross sectional area that decreases between the recycle duct entrance 340 and the recycle duct exit 345 designed to convey recycled fibers 12 at a velocity between about 5 n/s and about 10 n/s. Recycle duct entrance 340 can be placed proximal the scarfing roll 80 such that fibrous material scarfed from the article can be gathered into or directed to the recycle duct entrance 340 and conveyed towards the central recycle zone 275 and the portion of the edge zones 260 adjacent the central recycle zone 275. Fibrous material can be conveyed in the recycle duct 70 by air. The air pressure on the central recycle zone 275 and edge zones 260 adjacent the central recycle zone 275 can be lower than the pressure on the central scarfing zone 295 and the edge scarfing zones 315. The difference in pressure between these two zones creates a pressure differential across the recycle duct 70 in which the pressure at the recycle duct entrance 340 can be greater than the pressure at the recycle duct exit 345. The pressure differential across the recycle duct 70 results in air flow in the recycle duct 70 that can carry fibrous material to be re-deposited on the core pocket 50 as the core pocket 50 slides over the central recycle zone 275 and the edge zones 260 adjacent the central recycle zone 275. In addition to the pressure differential in the recycle duct 70 resulting from the different pressures on the zones of the air-distribution manifold 60, the scarfing roll 80 can impart momentum to the fibers 12 as the fibers 12 are scraped away from the outwardly facing free surface of the fibrous article 100 if the scarfing roll 80 rotates counter to the movement of the core pocket 50.

The air pressure on the central recycle zone 275 can be less than, the same, or more than the pressure on the central scarfing zone 295. The air pressure on the central recycle zone 275 can be less than, the same, or more than the pressure on the edge scarfing zone 315.

The process of forming an air-laid fibrous article can be thought of in terms of applying a series of pressures to different portions of the core pocket as the air-laid fibrous article is formed. The pressure applied at the central zone 240 can be thought of as a first pressure. The pressure applied at the edge zones 260 can be thought of as a second pressure. The pressure applied at the central recycle zone 275 can be thought of as a third pressure. The pressure applied at the central scarfing zone 295 can be thought of as a fourth pressure. The pressure applied at the edge scarfing zones 315 can be thought of as a fifth pressure. The pressure applied at the hold down zone 330 can be thought of as a sixth pressure.

Apparatus 10 can further comprise forming zone shields 370. Forming zone shields 370 can be configured such that as the core pocket 50 moves through the forming zone 1, the amount of air flow into the core pocket 50 from the surrounding environment is negligible. In other words, the core pocket 50 can be described as being in slideable and sealable engagement with the forming zone shields 370. The forming zone shields 370 can be comprised of any material that is impervious to air-flow and is suitable for use in high speed manufacturing operations. The seal between the forming zone shields 370 and the core pocket 50 can be comprised of horse hair fiber and felt. The seal between the forming zone shields 370 and core pocket 50 need not completely separate the core pocket 50 from the surrounding environment. Rather, the core pocket 50 can be separated from the surrounding environment in a manner sufficient to prevent unacceptable contamination of the air-laid fibrous article 100 from occurring during formation and to permit sufficient control of air pressures applied to different portions of the core pocket 50 by the air-distribution manifold 60.

Figure 13:
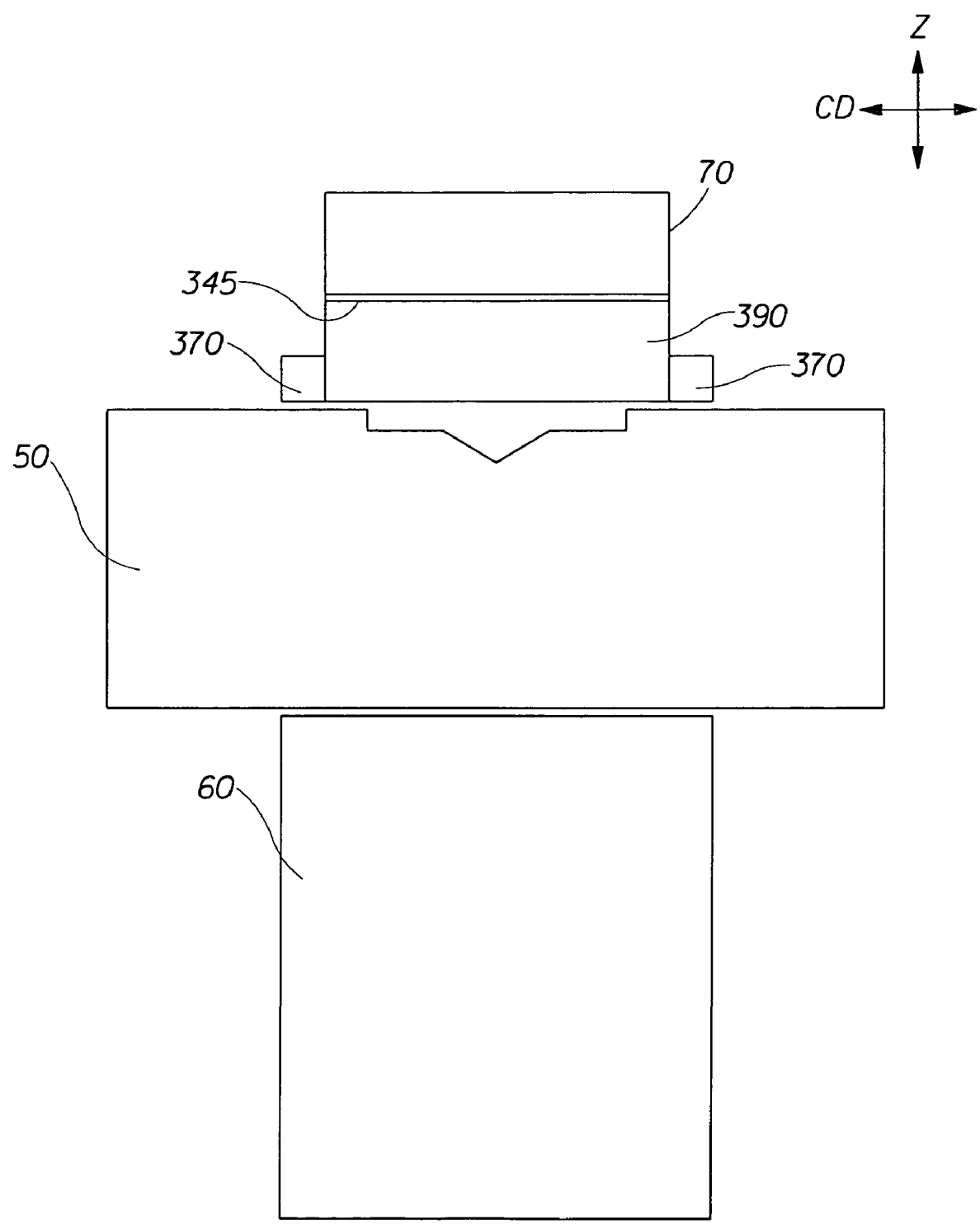
FIG. 13 is a cross sectional view of FIG. 1 looking upstream in the machine direction, as indicated by Section 13-13.

FIG. 13 illustrates a cross section, as marked in FIG. 1, in which the operative relationship between the forming zone shields 370, core pocket 50, air-distribution manifold 60, recycle duct exit 345, and recycle duct 70 are shown. As shown in FIG. 12 the forming zone shields 370 can be positioned to be in slideable and sealable relationship with the core pocket 50.

The drylap web 8 can be a web of cellulosic material such as wood pulp or other natural or synthetic fibers. In describing the fibers as being air-entrained, other gaseous mediums are also understood to be suitable.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for forming air-laid fibrous articles comprising:
   a core pocket, said core pocket comprising:
      a shield having an interior facing surface, an exterior facing surface, a shield first end, a shield second end opposing said shield first end, and a pair of opposing shield lateral side edges extending from said shield first end to said shield second end;
      a central opening defined by a void in said shield;
      a central forming chamber in air-flow communication with said central opening and having a central forming chamber periphery;
      a central foraminous forming surface in air-flow communication with said central forming chamber;
      a pair of edge openings extending along said shield and extending laterally beyond said shield lateral side edges;
      an edge forming chamber disposed about said central forming chamber periphery and in air-flow communication with said edge openings; and
      an edge foraminous forming surface in air-flow communication with said edge forming chamber.

2. The apparatus of claim 1, further comprising a plurality of central lateral baffles, said central lateral baffles spanning said central forming chamber and aligned about flush with said interior facing surface of said shield.

3. The apparatus of claim 1 further comprising a plurality of edge lateral baffles, said edge lateral baffles spanning said edge forming chamber and aligned about flush with said interior facing surface of said shield.

4. The apparatus of claim 1, wherein said shield is generally rectangular.

5. The apparatus of claim 1, wherein said pair of edge openings extend from said shield first end to said shield second end.

6. The apparatus of claim 1 wherein a portion of said central foraminous forming surface is recessed relative to said edge foraminous forming surface.

7. The apparatus of claim 1, further comprising an air-distribution manifold operatively related to said core pocket, said air-distribution manifold comprising:
   a central zone, said central zone having a central zone first end, a central zone second end opposing said central zone first end, and a pair of opposing central zone lateral side edges extending from said central zone first end to said central zone second end; and
   a pair of edge zones adjacent said central zone lateral side edges.

8. The apparatus of claim 7, wherein each said edge zone has an edge zone first end and an edge zone second end opposing said edge zone first end, wherein each said edge zone first end is aligned with said central zone first end.

9. The apparatus of claim 8, wherein each said edge zone second end is aligned with said central zone second end.

10. The apparatus of claim 7, wherein said air-distribution manifold further comprises a central recycle zone, said central recycle zone has a central recycle zone first end, a central recycle zone second end opposing said central recycle zone first end, and a pair of opposing central recycle zone lateral side edges extending from said central recycle zone first end to said central recycle zone second end, wherein said central recycle zone first end is adjacent said central zone second end.

11. The apparatus of claim 10, wherein each said edge zone has an edge zone first end and an edge zone second end opposing said edge zone first end, wherein said edge zone first end is aligned with said central zone first end and said edge zone second end is aligned with said central recycle zone second end.

12. The apparatus of claim 10, wherein said air-distribution manifold further comprises a central scarfing zone, said central scarfing zone has a central scarfing zone first end, a central scarfing zone second end opposing said central scarfing zone first end, and a pair of opposing central scarfing zone lateral side edges extending from said central scarfing zone first end to said central scarfing zone second end, wherein said central scarfing zone first end is adjacent said central recycle zone second end.

13. The apparatus of claim 12, wherein said air-distribution manifold further comprises a pair of edge scarfing zones adjacent said central scarfing zone lateral side edges.

14. The apparatus of claim 13, wherein each said edge scarfing zone has an edge scarfing zone first end and an edge scarfing zone second end opposing said edge scarfing zone first end, wherein said edge scarfing zone first end is aligned with said central scarfing zone first end.

15. The apparatus of claim 14, wherein said edge scarfing zone second end is aligned with said central scarfing zone second end.

16. The apparatus of claim 7, wherein said central zone and said edge zones are under pressure and the pressure in said central zone is negative and less than the pressure in said edge zones.

17. The apparatus of claim 12 further comprising a scarfing roll positioned in operative relationship with said central scarfing zone.

18. The apparatus of claim 17 further comprising a recycle duct having a recycle duct entrance and a recycle duct exit, said recycle duct entrance positioned in operative relationship with said scarfing roll and said recycle duct exit positioned in operative relationship with said central recycle zone.

19. The apparatus of claim 7, wherein said air-distribution manifold has an air-distribution surface that is curved.

20. The apparatus of claim 1, wherein said core pocket is shaped to form an absorbent article designed to be worn in proximity to the crotch of a wearer.

* * * * *

UNITED STATES PATENT AND TRADEMARK OFFICE
CERTIFICATE OF CORRECTION

| | |
|---|---|
| PATENT NO. | : 7,553,146 B2 |
| APPLICATION NO. | : 11/599789 |
| DATED | : June 30, 2009 |
| INVENTOR(S) | : Van Valkenburgh et al. |

It is certified that error appears in the above-identified patent and that said Letters Patent is hereby corrected as shown below:

Column 19

Line 56, after the number 5 delete "n" and insert --m--.

Line 56, after the number 10 delete "n" and insert --m--.

Signed and Sealed this

Seventeenth Day of November, 2009

David J. Kappos
*Director of the United States Patent and Trademark Office*